US005852224A

United States Patent [19]
Cooper et al.

[11] Patent Number: 5,852,224
[45] Date of Patent: Dec. 22, 1998

[54] α-LACTALBUMIN GENE CONSTRUCTS

[75] Inventors: Julian David Cooper, Blacksburg, Va.; Angelika Elisabeth Schnieke, Edinburgh, United Kingdom

[73] Assignee: PPL Therapeutics (Scotland) Limited, Edinburgh, United Kingdom

[21] Appl. No.: 381,691

[22] Filed: Jan. 31, 1995

[30] Foreign Application Priority Data

Dec. 15, 1994 [GB] United Kingdom ................... 9425326

[51] Int. Cl.$^6$ .......................... C12N 15/09; C12N 15/11; C12N 15/12; C12P 21/00
[52] U.S. Cl. ........................... 800/2; 435/69.1; 435/71.1; 435/172.3; 935/34; 935/52; 935/70
[58] Field of Search ................................. 800/2; 536/23.1, 536/24.1; 435/320.1, 240.2, 177.3, 69.1, 71.1; 350/365; 935/34, 52, 70

[56] References Cited

U.S. PATENT DOCUMENTS

| 4,293,583 | 10/1981 | Farr et al. | 426/657 |
|---|---|---|---|
| 5,530,177 | 6/1996 | Bleck et al. | 800/2 |

FOREIGN PATENT DOCUMENTS

| 0 014 3621 | 8/1980 | European Pat. Off. |
|---|---|---|
| WO 88/01648 | 3/1988 | WIPO . |
| WO 93/25567 | 12/1993 | WIPO . |
| WO 95/02692 | 1/1995 | WIPO . |
| WO 95/18224 | 7/1995 | WIPO . |

OTHER PUBLICATIONS

Stacey et al., "Use of Double–Replacement Gene Targeting To Replace the Murine α–Lactalbumin Gene with Its Human counterpart in Embryonic Stem Cells and Mice", *Molecular and Cellular Biology*, 14(2):1009–1016 (Feb. 1994).

Colman, A. (1996). American Journal of Clinical Nutrition 63, 6395–455.
Burdon, T. et al (1991). Mechanism of Development 36, 57–74.
Bleck, G. et al (1995). International Dairy Journal 5, 619–6320.
Kappel, C. et al (1992). Current Opinion: Biotechnology 3, 548–553.
Strojek, R. (1988). Generic Engineering: Principles and Methods v.10, pp. 221–246. Plenum Press.
Krimpenfort, P. et al (1991). Biotechnology 9, 844–847.
Hall, L. et al (1987) Biochem J. 242, 735–742.
Bleck, G.T. et al (1991) Symposium on Transgenes Development and Disease, Keystone Meeting, Tamarron, Colorado, J. Cell Biochem. Suppl. 0 (15 Part A), 198.
Adams, M et al (1993). Nature Genetics 4, 256–267.
Maschio, et al., "Transgenic Mice Carrying The Guinea–Pig α–Lactalbumin Gene Transcribe Milk Protein Genes In Their Sebaceouis Glands During Lactation", *Biochem. J.*, (1991) 275, 459–467.
Soulier, et al., "Expression Analysis Of Ruminant α–Lactalbumin IN Transgenic Mice: Developmental Regulation And General Location Of Important cis–Regulatory Elements", *FEBS Letters*, vol. 297, No. 1,2, (Feb. 1991) pp. 13–18.

(List continued on next page.)

*Primary Examiner*—Brian R. Stanton
*Attorney, Agent, or Firm*—Seidel, Gonda, Lavorgna & Monaco, PC

[57] ABSTRACT

The present invention utilizes genetic engineering techniques to prepare non-human transgenic mammals that express human α-lactalbumin in their milk at a concentration of 2 mg/ml or greater. The invention also includes methods of preparing human α-lactalbumin in, for example, mice and cows. Also taught are methods for preparing human α-lactalbumin in which from one to four of its natural phenylalanine residues have been substituted by another amino acid.

5 Claims, 20 Drawing Sheets

OTHER PUBLICATIONS

Hochi, et al., "Secretion Of Bovine α–Lactalbumin Into The Milk Of Transgenic Rats", *Molecular Reproduction And Development* 33: 160–164 (1992).

Vilotte, et al., "Efficient Tissue–Specific Expression Of Bovine α–Lactalbumin In Transgenic Mice", *Eur. J. Biochem.* 186, 43–48 (1989).

Ninomiya, et al., "Functions Of Milk Protein Gene 5' Flanking Regions On Human Growth Hormone Gene", *Molecular Reproduction And Development* 3&:276–283 (1994).

F. Maynard, *Journal of Dairy Research,* vol. 59, No. 3, "Identification of a new molecular form of human alpha–lactalbumin" pp. 425–429 (1992).

Hochi Shin–Ichi et al., *Molecular Reproduction and Development,* vol. 33, "Secretion of bovine alpha–lactalbumin into the milk of transgenic rates", pp. 160–163, (1992).

Jean–Luc Vilotte et al., *Biochimie,* vol. 69, No. 6/7, "Complete nucleotide sequence of bovine alpha–lactalbumin gene: comparison with its rat counterpart", pp. 609–620 (1987).

Ba-2
5'GCGGGATCCACAACTGAAGTGACTTAGC 3'   NC
       BamHI

Ba-7
5'GATGGATCCTGGGTGGTCATTGAAAGGACTGATGC 3'   C
      BamHI

Ba-8
5'GCAGGCGAATTCCTCAAGATTCTGAAATGGGGTCACCACACTG 3'   NC
        EcoRI    StuI

Ba-9
5'GAGGATCC AATGTGTATCTGGCTATTAGTGG 3'   C
     BamHI

C = primer complementary to coding strand
NC = primer complementary to non-coding strand

FIG. 1

PKU-1

Phe → Tyr

5'GCTGAATTCGTTAACAAAATGTGAGGTGTATCGGGAGCTGAAAGAC3'     C

EcoRI Hpal           aa 9

PKU-2

Phe → Tyr

5'GCGGATCCGATCGCTTGTGTCATAACCACTGGTATGGTACGCGGTACAGACCCCTG3'     NC

BamHI PvuI               aa 31

PKU-2L

Phe → Leu

5'GCGGATCCGATCGCTTGTGTCATAACCACTGGTATGGAGCGGGTACAGACCCCTG3'     NC

BamHI PvuI               aa 31

PKU-3

Phe → Tyr

5'GCGGATCCGATCGTACAAAACAATGACAGCACAGAATATGGACTCTACCAGATAAATAAAATTTGG3'     C

BamHI PvuI                      aa 53

PKU-4

Phe → Tyr

5'GCTCTAGATCATCATCCAGGTACTCTGGCAGGAG3'     NC

XbaI Bsa-BI     aa 80

FIG. 10A

PKU-5
5'GCTGAAGCTTCACTTACTTCACTC3'
       HindIII

PKU-6
                                 Stop, Arg, Arg, Arg, Arg, Arg,Leu......
5'GCGGATCCAAAGACAGCAGGTGTTCACCGTCGACGACGCCTACGTAACTTCTCACAGAGCCACTG3'
   BamHI             BspMI            SalI (6 x ARG)
                                                 HincII

PKU-7
                                  Phe → Ser
5'GCTGAATTCGTTAACAAAATGTGAGGTGAGCCGGGAGCTGAAAGAC3'
    EcoRI  HpaI                 aa 9

PKU-8
                                                      Phe → Tyr
5'GCGGATCCGATCGCTTGTGTGTCATAACCACTGGTATGATACGCGGGTACAGACC3'
   BamHI  PvuI                             aa 31

PKU-9
                                                                Phe → Leu
5'GCGGATCCGATCGTACAAAAACAATGACAGCACAGAATATGGACTCCTCCAGATAAATAAAATTTGG3'
   BamHI  PvuI                                                     aa 53

PKU-10   Phe → Leu
5'GCTCTAGATCATCATCCAGCAGCTCTGGCAGGAG3'
   Xbal   Bsa-BI      aa 80 c = primer complementary to coding strand
NC = primer complementary to non-coding strand

FIG. 10C

α-lac^m/α-lac^m

α-lac^m/α-lac^-

α-lac^-/α-lac^-

SEQUENCE LISTING ( 1 ) GENERAL INFORMATION:

( i i i ) NUMBER OF SEQUENCES: 17

( 2 ) INFORMATION FOR SEQ ID NO: 1:

( i ) SEQUENCE CHARACTERISTICS:
       ( A ) LENGTH: 27 base pairs
       ( B ) TYPE: nucleic acid
       ( C ) STRANDEDNESS: single
       ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO: 1:

GCGGATCCAC AACTGAAGTG ACTTAGC                                        27

( 2 ) INFORMATION FOR SEQ ID NO: 2:

( i ) SEQUENCE CHARACTERISTICS:
       ( A ) LENGTH: 35 base pairs
       ( B ) TYPE: nucleic acid
       ( C ) STRANDEDNESS: single
       ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO: 2:

GATGGATCCT GGGTGGTCAT TGAAAGGACT GATGC                               35

( 2 ) INFORMATION FOR SEQ ID NO: 3:

( i ) SEQUENCE CHARACTERISTICS:
       ( A ) LENGTH: 43 base pairs
       ( B ) TYPE: nucleic acid
       ( C ) STRANDEDNESS: single
       ( D ) TOPOLOGY: linear ( i i ) MOLECULE TYPE: cDNA ( x i ) SEQUENCE DESCRIPTION: SEQ ID NO: 3:

GCAGGCGAAT TCCTCAAGAT TCTGAAATGG GGTCACCACA CTG                      43

( 2 ) INFORMATION FOR SEQ ID NO: 4:

( i ) SEQUENCE CHARACTERISTICS:
       ( A ) LENGTH: 33 base pairs
       ( B ) TYPE: nucleic acid
       ( C ) STRANDEDNESS: single
       ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO: 4:

GAGGATCCAA TGTGGTATCT GGCTATTTAG TGG                                 33

( 2 ) INFORMATION FOR SEQ ID NO: 5:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO: 5:

GCTGAATTCG TTAACAAAAT GTGAGGTGTA TCGGGAGCTG AAAGAC                           46

( 2 ) INFORMATION FOR SEQ ID NO: 6:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO: 6:

GCGGATCCGA TCGCTTGTGT GTCATAACCA CTGGTATGGT ACGCGGTACA GACCCCTG             58

( 2 ) INFORMATION FOR SEQ ID NO: 7:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO: 7:

GCGGATCCGA TCGCTTGTGT GTCATAACCA CTGCTATGGA GCGCGGTACA GACCCCTG             58

( 2 ) INFORMATION FOR SEQ ID NO: 8:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO: 8:

GCGGATCCGA TCGTACAAAA CAATGACAGC ACAGAATATG GACTCTACCA GATAAATAAT           60

AAAATTTGG                                                                   69

( 2 ) INFORMATION FOR SEQ ID NO: 9:

( i ) SEQUENCE CHARACTERISTICS:
    ( A ) LENGTH: 34 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO: 9:

GCTCTAGATC ATCATCCAGG TACTCTGGCA GGAG 34

( 2 ) INFORMATION FOR SEQ ID NO: 10:

( i ) SEQUENCE CHARACTERISTICS:
      ( A ) LENGTH: 24 base pairs
      ( B ) TYPE: nucleic acid
      ( C ) STRANDEDNESS: single
      ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO: 10:

GCTGAAGCTT CACTTACTTC ACTC 24

( 2 ) INFORMATION FOR SEQ ID NO: 11:

( i ) SEQUENCE CHARACTERISTICS:
      ( A ) LENGTH: 65 base pairs
      ( B ) TYPE: nucleic acid
      ( C ) STRANDEDNESS: single
      ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO: 11:

GCGGATCCAA AGACAGCAGG TGTTCACCGT CGACGACGCC TACGTAACTT CTCACAGAGC 60

CACTG 65

( 2 ) INFORMATION FOR SEQ ID NO: 12:

( i ) SEQUENCE CHARACTERISTICS:
      ( A ) LENGTH: 46 base pairs
      ( B ) TYPE: nucleic acid
      ( C ) STRANDEDNESS: single
      ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO: 12:

GCTGAATTCG TTAACAAAAT GTGAGGTGAG CCGGGAGCTG AAAGAC 46

( 2 ) INFORMATION FOR SEQ ID NO: 13:

( i ) SEQUENCE CHARACTERISTICS:
      ( A ) LENGTH: 54 base pairs (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 13:

GCGGATCCGA TCGCTTGTGT GTCATAACCA CTGGTATGAT ACGCGGTACA GACC     54

(2) INFORMATION FOR SEQ ID NO: 14:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 14:

GCGGATCCGA TCGTACAAAA CAATGACAGC ACAGAATATG GACTCCTCCA GATAAATAAT     60

AAAATTTGG     69

(2) INFORMATION FOR SEQ ID NO: 15:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 15:

GCTCTAGATC ATCATCCAGC AGCTCTGGCA GGAG     34

(2) INFORMATION FOR SEQ ID NO: 16:

(i) SEQUENCE CHARACTERISTICS:
        (A) LENGTH: 3952 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 16:

GGATCCAAAG TTGGCTAAAC ACTGGCCGGG TGCAGTGCTT CCACCTGTAA TTCCAGCACT     60

TTGGAAGGCT GAGGTGGGCA GATTGCTTGA GGTCAGGAGT TGAGACCAG CTTGGCTAAC     120

AGCAAAACCC TGTCTCTACC AAAAGTACAA AAATTATCTG GGTGTGGTGG CAGGCGCCTG     180

TAATCCCAGC TACTCGGGAG GCTGAGGCAG AAGAATTGTT TGAACCTGGG AGGCAGAGGT     240

TGTAGTGAGC TGAGATCGCT CATTNNNNNN NNNNNNNNNN NNNNNNNNNN NNNNNNNNNN     300

| | | | | | | |
|---|---|---|---|---|---|---|
| NNNNNNNNNN | NNNNNNNNNN | NNNNNNNNNN | NNNNNNNNNN | NNNNNNNNNN | NNNNNNNNNN | 360 |
| NNNNNNNNNN | NNNNNNNNNN | NNNNNNNNNN | NNNNNNNNNN | NNNNNNNNNN | NNNNNNNNNN | 420 |
| NNNNNNNNNN | NNNNNNNNNN | NNNNNNNNNN | NNNNNNNNNN | NNNNNNNNNN | NNNNNNNNNN | 480 |
| NNNNNNNNNN | NNNNNNNNNN | NNNNNNNNNN | NNNNNNNNNN | NNNNNNNNNN | NNNNNNNNNN | 540 |
| NNNNNNNNNN | NNNNNNNNNN | NNNNNNNNNN | NNNNNNNNNN | NNNNNNNNNN | NNNNNNNNNN | 600 |
| NNNNNNNNNN | NNNNNNNNNN | NNNNNNNNNN | NNNNNNNNNN | NNNNNNNNNN | NNNNNNNNNN | 660 |
| NNNNNNNNNN | NNNNNNNNNN | NNNNNNNNNN | NNNNNNNNNN | NNNNNNNNNN | NNNNNNNNNN | 720 |
| NNNNNNNNNN | NNNNNNNNNN | NNNNNNNNNN | NNNNNNNNNN | NNNNNNNNNN | NNNNNNNNNN | 780 |
| NNNNNNNNNN | NNNNNNNNNN | NNNNNNNNNN | NNNNNNNNNN | NNNNNNNNNN | NNNNNNNNNN | 840 |
| NNNNNNNNNN | NNNNNNNNNN | NNNNNNNNNN | NNNNNNNNNN | NNNNNNNNNN | NNNNNNNNNN | 900 |
| NNNNNNNNNN | NNNNNNNNNN | NNNNNNNNNN | NNNNNNNNNN | NNNNNNNNNN | NNNNNNNNNN | 960 |
| NNNNNNNNNN | NNNNNNNNNN | NNNNNNNNNN | NNNNNNNNNN | NNNNNNNNNN | NNNNNNNNNN | 1020 |
| NNNNNNNNNN | NNNNNNNNNN | NNNNNNNNNN | NNNNNNNNNN | NNNNNNNNNN | NNNNNNNNNN | 1080 |
| NNNNNNNNNN | NNNNNNNNNN | NNNNNNNNNN | NNNNNNNNNN | NNNNNNNNNN | NNNNNNNNNN | 1140 |
| NNNNNNNNNN | NNNNNNNNNN | NNNNNNNNNN | NNNNNNNNNN | NNNNNNNNNN | NNNNNNNNNN | 1200 |
| NNNNNNNNNN | NNNNNNNNNN | NNNNNNNNNN | NNNNNNNNNN | NNNNNNNNNN | NNNNNNNNNN | 1260 |
| NNNNNNNNNN | NNNNNNNNNN | NNNNNNNNNN | NNNNNNNNNN | NNNNNNNNNN | NNNNNNNNNN | 1320 |
| NNNNNNNNNN | TCTTTTTCAA | TTATTCATTT | GTTACAGTGG | GTTATGATAC | AAATGTTTAT | 1380 |
| AGATGCCTAC | TCTGTACTAG | TACTACAGAG | CAGTTTTTCT | GTGTTTATAT | TCAGTTCAAT | 1440 |
| TGTAGTGTGT | TGAGTTGTAT | WWTAATCCAT | GTATTAAATC | AAATAAACAA | ACAAAATGCC | 1500 |
| ATGTTCTTTG | GTACAAGCAA | CACTCACCAA | AGGCATTTGG | GGTCTGCATT | TGGAATTCTC | 1560 |
| AGGCAAACTC | TCTCTTGTTC | CTAGTCTGTA | CTTATTTTCC | CCACACTAGC | TTATGTATAT | 1620 |
| ATATTTTTGA | GATTGGAGTT | GCCCTTGTTG | CCCAGGCTGG | AGTGCAGTGG | CACGATTCTT | 1680 |
| GGCTCACGAG | ACCTCCACGT | CTTGGGTTAA | AGCGTTTCTC | CTGCCTCAGC | CTCCTGACTA | 1740 |
| CTGGGATTAC | AGGCGCCTGC | CACCATGCCC | GGCTAATTTT | TGTATTTTTA | GTAGAGATGG | 1800 |
| GCTTTCACCA | TGTTGCTCAG | GCTGGTCTTG | AAACTCCCCA | CCTCGGCCCT | TCCCAAATGC | 1860 |
| GCTGGGATTA | CAGGTGTGAG | CCACAGTGCC | TGGCCTGTAC | ATTTTTAAA | TTTCAATGTC | 1920 |
| TAATATGGTG | TCCACTGAAT | TAAGAATTCT | TTTGAGAAAA | TGAATCAATA | AATCTATACA | 1980 |
| CTGCCTCCTT | TATCCAGTGA | GGTATGGCTG | GATCAGCTTC | ATGACATACA | TGCCAGTAGT | 2040 |
| TCTCCTCCTC | CTCCTTTTTT | ACAAATAAAA | ATTGTATATG | TTGAAGGTGT | ACAACTTGAT | 2100 |
| GTTTGTTATA | TGTATACACT | TAAATGTCAC | CACNNNNNNN | NNNNNNNNNN | NNNNNNNNNN | 2160 |
| NNNNNNNNNN | NNNNNNNNNN | NNNNNNNNNN | NNNNNNNNNN | NNNNNNNNNN | NNNNNNNNNN | 2220 |
| NNNNNNNNNN | NNNNNNNNNN | NNNNNNNNNN | NNNNNNNTT | TGGGTAGAAG | CAGACAGTAA | 2280 |
| ACTTGCTGTT | CTCTTCCTGA | GATCTTTGT | TGAGATGCTG | AATAGGAGGC | AGCATGGCAG | 2340 |
| CTGAGCTATC | TGTTCTGCTT | TCTCTACCTC | TGTCTCTTTC | CCTTAGGCCT | AAAATGAAGC | 2400 |
| TCTAAGCCAA | GCAAAGGTCT | GAAGTCATCC | AGACTAATTG | GGAAGCGGGT | AGGCTCCAGG | 2460 |
| GAGTGGCTCT | CAGAGAGCAG | ACCATTTACT | GAGCTCNNNN | NNNNNNNNNN | NNNNNNNNAA | 2520 |
| TACAGAGTTT | TGTTCTCTAC | TCTTATCCTG | CTTTCTCCTC | CCTGCTACTT | TTCCCTGACA | 2580 |
| CCTATCTTGT | TGTGAAGACA | GGAATTGCAT | TAGATAAAAT | CAAATCTTTT | TTATTTTTTT | 2640 |
| TTGAGATGGA | ATCTTGCTCT | GTTTCCAGGC | TGGAGTGCTG | NNNNNNNNNN | NNNNNNNNNN | 2700 |

| | | | | | | |
|---|---|---|---|---|---|---|
| NNNNNNNNN | NNNNNNNNN | NNNNNNNNN | NNNNNNNNN | NNNNNNNNN | NNNNNNNNN | 2760 |
| NNNNNNNNN | NNNNNNNNN | NNNNNNNNN | NNNNNNNNN | NNNNNNNNN | NNNNNNNNN | 2820 |
| NNNNNNNNN | NNNNNNNNN | NNNNNNNNN | NNNNNNNNN | NNNNNNNNN | NNNNNNNNN | 2880 |
| NNNNNNNNN | NNNNNNNNN | NNNNNNNNN | NNNNNNNNN | NNNNNNNNN | NNNNNNNNN | 2940 |
| NNNNNNNNN | NNNNNNNNN | NNNNNNNNN | NNNNNNNNN | NNNNNNNNN | NNNNNNNNN | 3000 |
| NNNNNNNNN | NNNNNNNNN | NNNNNNNNN | NNNNNNNNN | NNNNNNNNN | NNNNNNNNN | 3060 |
| NNNNNNNNN | NNNNNNNNN | NNNNNNNNN | NNNNNNNNN | NNNNNNNNN | NNNNNNNNN | 3120 |
| NNNNNNNNN | NNNNNNNNN | NNNNNNNNN | NNNNNNNNN | NNNNNNNNN | NNNNNNNNN | 3180 |
| NNNNNNNNN | NNNNNNNNN | NNNNNNNNN | NNNNNNNNN | NNNNNNNNN | NNNNNNNNN | 3240 |
| NNNNNNNNN | NNNNNNNNN | NNNNNNNNN | NNNNNNNNN | NNNNNNNNN | NNNNNNNNN | 3300 |
| NNNNNNNNN | NNNNNNNNN | NNNNNNNNN | NNNNNNNNN | NNNNNNNNN | NNNNNNNNN | 3360 |
| NNNNNNNNN | NNNNNNNNN | NNNNNNNNN | NNNNNNNNN | NNNNNNNNN | NNNNNNNNN | 3420 |
| NNNNNNNNN | NNNNNNNNN | NNNNNNNNN | NNNNNNNNN | NNNNNNNNN | NNNNNNNNN | 3480 |
| ATCTGGTCAG | CAGTGAAGCT | CAGTGTACAC | ATTCATTCCT | TCCTTCACTG | CTTGATTTGT | 3540 |
| CACCAAGTGG | TTATTGAGGA | TATGCTGTTT | GCTAGGTACT | ACTTACTTA | TTTATTTGTT | 3600 |
| TATTTAGAGA | TGGGGTCTCA | CAATGTTGCC | CAGTCTACAG | GACAGTGGCT | ATTCACAGGT | 3660 |
| GTGAGCACAG | CACACTACAG | CCTCAAACTC | CTGAGTTCAA | GAGATCCTCC | TGCCTCAGTC | 3720 |
| TCTCGAGTAG | CTGGGACTAC | AGGGATGTGC | CACCACACAT | GGCTTAGGCT | CTACTTTAGC | 3780 |
| TGCTACTTGA | AGGATGAAGA | TAGGAGGAGA | CACTCTTATT | TTATTTGATT | TCTTTTTTTT | 3840 |
| TTTTTTTTTT | TTGACAGAGT | TTTGCTCTGT | TGCCAGGCTG | GAGTGCTCAC | TGCAACCTCC | 3900 |
| ACCTCCAGGT | CAAGCAATTC | TCCTGCTCAG | CCTCCGAGTA | GTCGGACCAA | GG | 3952 |

( 2 ) INFORMATION FOR SEQ ID NO: 17:

( i ) SEQUENCE CHARACTERISTICS:
        ( A ) LENGTH: 2119 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO: 17:

| | | | | | | |
|---|---|---|---|---|---|---|
| GGAATTCCCA | TTCCTGTCGT | GTACCCTTGC | AGTGCCTCTG | GGTGGAATGC | GGAGAAATGG | 60 |
| AGTGGCTCCA | CTTCTGTTGT | GTTTCTGAAC | ATGTATCTCT | TGCTATCAGA | ACTTTCTGCT | 120 |
| CATCCCTTCT | GGCACACCAA | GATCCTCCAC | ATTCCCTTCA | CTCATGCCAC | TTCATATACT | 180 |
| GGTTATCCAT | GGTACAGAAG | ACAGGATTTA | ACTGAGAGGA | CTTTTCCCTG | ACTCTGAATA | 240 |
| CATGTAGGAG | ATAACGATAT | GGAAGACCTT | CAGTATGTAA | GTCTTAAATA | GATTGGTTGG | 300 |
| GATAAATGTT | CCCTGAAACA | TAAGAAACAG | CGCAGCGGCT | CCTGTCTGTA | ATCTAGCACT | 360 |
| TTGGGAGGGC | CGAGGCAGG | CAGGCAAATT | GCCTGAGCTC | AGAAGTTTGA | GACCAGCCTG | 420 |
| GCCAACATGC | AGAAACTCCG | TCTCTACTAA | AAATACATAA | ATTAACCGGG | CATGGTAACA | 480 |
| CGTGCCTGTA | GTCCCAGCTA | CTCGGGAGGC | TGAGGCAGGA | GAATCACTTG | AGCCTGGGAG | 540 |
| GCAGAGGTTG | CAGTGAGCCA | AGATCGCGCC | ACTGCATTCC | AGCCTGGGCA | ACAGAGTGAG | 600 |

-continued

| | | | | | | |
|---|---|---|---|---|---|---|
| ACTTGGTCAA | AAAAAAAAAA | AAAAAAAAAA | AAAAGGAAGA | AGAAGAAGAA | ATCAGGTTTA | 660 |
| GAGATGAGGA | CAAAGAAGAC | GAATCGGTGG | CATGAAGGAG | CTAAGAGCTA | CTTGTCACCA | 720 |
| TGACATGAAG | CTTCATGCCA | GCAAATTAAA | GGAGCTATTC | AGAACTAGTA | TCCTCAACTC | 780 |
| TACTTGCTCA | GGGGCACTGA | CCTTATAGAG | ATTCCAGACA | TAAGCTTGTT | CAGCCTTAAG | 840 |
| TCCAATCTTT | CCACTGGCTT | GGTCCTTCCC | ACTTTCTGTG | GCCAACTCTG | AGGTTGTCTA | 900 |
| CAAGTTATTG | GTCTTAGATT | TATGTAATGT | CTCAATGCCA | GTGTAGTATT | TGGTTATTTA | 960 |
| CGGTAGGAGT | GGTTAGGGGT | GGGGAATCTG | ATAATAGCTC | GTAGGATAGC | TAGATTCTTT | 1020 |
| TTTTTTTTTT | TTTTTTTTAA | AGATAGGGTC | TCACTTTGTC | TCCCAGGATG | GATGGATGGA | 1080 |
| GTGCAGTGGA | GTGAACATGG | CTCACTGCAG | CCTCGACCTC | CTGTGCTCAA | GTGTTCCTCC | 1140 |
| TGCCTCAGCC | CCTCAAGTAG | CTGGGACTAC | AGGCACATGT | CACCATGCCC | AGCTAATTTT | 1200 |
| TTTTGTAGAG | ATGGGATTTT | ACCATGTTGC | CCAGGCTGGT | CTCGAGCTCC | TGGGCTCAAG | 1260 |
| TGATCCACCA | GACTCGGCCT | CCCAAAATGC | CGGGATTACA | GGTGTGAGCC | ACTGTGCCTG | 1320 |
| GCCTAGATGC | TTTCATACAG | GCTTTTCAAT | TATGCATTTT | CCTTAAGTAG | GAAGTCTTAA | 1380 |
| GATCCAAGTT | ATATCGGATT | GTTGTAGTCT | ACGTTCCCAT | ATTCTATTCC | TATTTCTGAG | 1440 |
| CCTTCAGTCA | TGAGCTACCA | TATTAAAGAA | CTAATTCTGG | GCCTTGTTAC | ATGGCTGGAT | 1500 |
| TGGTTGGACA | AGTGCCAGCT | CTGATCCTGG | GACTGTGGCA | TGTGATGACA | TACACCCCCT | 1560 |
| CTCCACATTC | TGCATGTCTC | TAGGGGGGAA | GGGGAAGCT | CGGTATAGAA | CCTTTATTGT | 1620 |
| ATTTTCTGAT | TGCCTCACTT | CTTATATTGC | CCCCATGCCC | TTCTTTGTTC | CTCAAGTAAC | 1680 |
| CAGAGACAGT | GCTTCCCAGA | ACCAACCCTA | CAAGAAACAA | AGGGCTAAAC | AAAGCCAAAT | 1740 |
| GGGAAGCAGG | ATCATGGTTT | GAACTCTTTC | TGGCCAGAGA | ACAATACCTG | CTATGGACTA | 1800 |
| GATACTGGGA | GAGGGAAAGG | AAAAGTAGGG | TGAATTATGG | AAGGAAGCTG | GCAGGCTCAG | 1860 |
| CGTTTCTGTC | TTGGCATGAC | CAGTCTCTCT | TCATTCTCTT | CCTAGATGTA | GGGCTTGGTA | 1920 |
| CCAGAGCCCC | TGAGGCTTTC | TGCATGAATA | TAAATAAATG | AAACTGAGTG | ATGCTTCCAT | 1980 |
| TTCAGGTTCT | TGGGGGTAGC | CAAAATGAGG | TTCTTTGTCC | CTCTGTTCCT | GGTGGGCATC | 2040 |
| CTGTTCCCTG | CCATCCTGGC | CAAGCAATTC | ACAAAATGTG | AGCTGTCCCA | GCTGCTGAAA | 2100 |
| GACATAGATG | GTTATGGAG | | | | | 2119 |

α-LACTALBUMIN GENE CONSTRUCTS

FIELD OF THE INVENTION

The present invention is concerned with recombinant gene constructs for expressing the protein α-lactalbumin, or functional equivalents or parts thereof.

BACKGROUND OF THE INVENTION

Human milk has been shown to be superior over other milk types, notably cow, sheep, camel and goat milk, for human infant nutrition. However, many mothers find breast feeding difficult or inconvenient. Moreover, in countries where infant food supplements are in great demand, it would be highly desirable to be able to supply a milk product with the nutritional benefits of human milk.

One of the major differences of human milk over milk from other mammals (for example cows or sheep) is the presence of α-lactalbumin as the major whey protein. Whilst α-lactalbumin is present in other milk types, the concentration is relatively low and instead the major whey protein is β-lactoglobulin. The level of α-lactalbumin varies from species to species, with human milk containing about 2.5 mg/ml, cow milk 0.5–1.0 mg/ml and mouse milk 0.1–0.8 mg/ml.

The gene sequences encoding for the bovine α-lactalbumin and for the human α-lactalbumin proteins have been elucidated and the sequence information published by Vilotte et al, in Biochemie 69:609–620 (1987) and by Hall et al, in Biochem J 242: 735–742 (1987), respectively.

SUMMARY OF THE INVENTION

The present invention seeks to utilise genetic engineering techniques to provide a recombinant gene construct capable of producing an α-lactalbumin concentration of greater than 1.0 mg/ml, for example 1.2 mg/ml or above, in milk when expressed in mammalian cells. Generally said construct is adapted to be expressed in non-human animal, especially bovine, cells.

In one aspect, the present invention provides a recombinant expression system adapted to express α-lactalbumin, or a functional equivalent or part thereof in cells of a non-human, preferably bovine, animal. Preferably, the recombinant expression system of the present invention is adapted to express the human α-lactalbumin protein, or a functional equivalent or part thereof.

The term "expression system" is used herein to refer to a genetic sequence which includes a protein-encoding region and is operably linked to all of the genetic signals necessary to achieve expression of the protein encoding region. Optionally, the expression system may also include a regulatory element, such as a promoter or enhancer, to increase transcription and/or translation of the protein-encoding region, or to provide control over expression. The regulatory element may be located upstream or downstream of the protein-encoding region, or may be located at an intron (non-coding portion) interrupting the protein encoding region. Alternatively it is also possible for the sequence of the protein-encoding region itself to comprise a regulatory ability.

The term "functional equivalent" refers to any derivative which is functionally substantially similar to the reference sequence or protein. In particular the term "functional equivalent" includes derivatives in which nucleotide base(s) and/or amino acid(s) have been added, deleted or replaced without a significantly adverse effect on biological function, especially biological function in milk production.

Genetic engineering has been recognised as a powerful technique not only in research but also for commercial purposes. Thus, by using genetic engineering techniques (see Maniatis et al Molecular Cloning, a Laboratory Manual Cold Spring, Harbor Laboratory, Cold Spring Harbor, N.Y. 1982 and "Principle of Genetic Engineering", Old and Primrose, 5th edition, 1994, both incorporated herein by reference) exogenous genetic material can be transferred to a host cell and the protein or polypeptide encoded by the exogenous genetic material may be replicated by and/or expressed within the host. For the purposes of simplicity genetic engineering is normally carried out with prokaryotic micro-organisms, for example bacteria such as *E. coli*, as host. However, use has also been made of eukaryotic organisms, in particular yeasts or algae, and in certain applications eukaryotic cell cultures may also be used.

Genetic alterations to mammalian species by microinjection of genes into the pro-nuclei of single-cell embryos has been described by Brinster et al, in Cell 27: 223–231, 1981. Here the foreign genetic material is introduced into the fertilised egg of an animal which then proceeds to develop into an embryo in the normal manner having been transplanted into a foster mother. Truly transgenic animals contain copies of the exogenous DNA in each cell.

Where the injected genetic material is successfully incorporated into the host chromosome the animal is termed "transgenic" and the transgene is inherited in the normal Mendelian manner. However, only a low proportion of gene transfer operations are successful, especially for large domestic animals such as pigs, sheep and cattle. To date it has not been possible to control the location at which the transgene integrates into the host chromosome for such animals.

For the purpose of the present invention it may, in certain circumstances, be sufficient simply to produce a "mosaic" donor animal. In this situation the transgene is incorporated into the chromosome copies of only certain body organs. Mosaic animals are generally produced by introducing exogenous DNA into an embryo at a later developmental stage.

One of the most promising application of transgenesis in livestock aims to utilise the mammary gland as a "bioreactor" to produce recombinant proteins of pharmaceutical or nutritional interest in milk. The mammary gland is an attractive organ in which to express heterologous proteins due to its capacity to produce large quantities of protein in an exocrine manner. Recombinant DNA techniques may be used to alter the protein composition of cow'milk used for human or animal consumption. For example, the expression of human milk proteins in cow'milk could improve its nutritional value in infant formula applications (Strijker et al, in Harnessing Biotechnology for the 21st Century, ed Ladisch and Boser, American Chemical Society, Pages 38-21 (1992)). Both applications would benefit from ability to increase production capacity inexpensively by multiplying producer animals with conventional and advanced breeding techniques.

The first step in developing a transgene to be expressed in the mammary gland is to clone the gene for the protein of interest. To direct expression into milk, the promoter gene for a major milk protein expressed in milk is employed. Milk protein genes are tightly regulated and are not expressed in tissues other than the mammary gland, a characteristic that minimises the possibility of negative effects on the animal from inappropriate expression in other tissues. Among the regulatory genes used to express heterologous proteins in the mammary gland are alpha-$S_1$-casein (Strijker et., 1992, supra), beta-lactoglobulin (Wright et al., Bio/Technology 9:831–834 (1991)) whey acidic protein (Ebert and Schindler, Transgenic Farm animals: Progress Report (1993)) and beta-casein (Ebert and Schindler, 1993, supra).

Newly-made gene constructs are normally tested in transgenic mice before adopting them for use in cattle. Milk obtained from the transgenic mice is assayed for quantity of recombinant protein. If enough milk is available, the protein may be isolated to examine its structural characteristics and bioactivity. The selection of a particular construct for use in cattle will depend primarily on consideration of both expression level and authenticity of the resultant recombinant protein. Transgenesis is cattle in normally initiated by microinjecting several hundred copies of gene construct into one of the two pronuclei in a zygote. Zygotes may be obtained in vivo from the oviducts (Roschlau et al., Arch Tierz. Berlin 31:3–8 (1988); Roschlau et al., in J. Reprod. Fertil. (suppl 38), Cell Biology of Mammalian Egg Manipulation, ed Greve et al (1989); Hill et al., Theriogenology 37:222 (1992); Bowen et al. Biol Reprod. 50:664-448 (1994)) or by in vitro fertilisation of in vitro matured oocytes (Krimpenforth et al., Biotechnology 9:844–847 (1991); Hill et al., 1992, supra; Bowen et al., 1993 supra). Bovine zygotes must be centrifuged at 15,000×g for several minutes to displace opaque lipid in order to visualise the pronuclei with phase contrast, Nomarski or Hoffman interference contrast optics. 2–4 pl of buffer containing several hundred copies of DNA construct are injected into a pronucleus. Transgenes are thought to integrate into random breaks in chromosomal DNA that result from mechanical disruption during the microinjection process. Ideally, the transgenes integrate at the zygote stage prior to DNA replication to ensure that every cell in the adult contains the transgene. In general, several "copies" of the transgene, linked together linearly, integrate in a single site on a single chromosome. The site of integration is random. Integration probably occurs after the first round of DNA replication, and perhaps as late as the 2- or 4-cell stage (Wall and Seidel, 1992), resulting in animals that are mosaic with respect to the transgene. Indeed, up to 30% of animals in which transgenes are detected in somatic tissues do not transmit the transgenes to their offspring (or transmit to less than the expected 50%).

After microinjection, embryos are either transferred directly into the oviducts of recipients or cultured for a few days and transferred to the uterus of recipient cattle. Confirmation of transgene integration is obtained by Southern blot analysis of tissues sampled from the calf after birth. Transgene expression is measured by assaying for the gene product in appropriate tissues, or in this case milk. Embryo survival after microinjection, transgene integration frequency, frequency of expression and expression level, and frequency of germline transmission vary according to quantity and quality of DNA construct injected, strain of mice used (Brinster et al., Pr0c. Natl. Acad Sci. USA 82:4438–4442 (1985)) and skill and technique of the operator performing microinjection. This basic approach has been routinely applied to produce transgenic sheep (Wright et al., 1991, supra), goats (Ebert and Schindler, 1993, supra) pigs (Rexroad and Purcel, Proc 11th Intl. Congr. Anim. Reprod. A. I. Dublin 5:29–35 (1988)) and cattle (Krimpenfort et al., 1991, supra; Hill et al., 1992, supra; Bowen et al., 1994, supra).

Reference is also made to WO-A-88/01648 (of Immunex Corporation), to WO-A-88/00239 and to WO-A-90/05188 (both of Pharmaceutical Proteins Limited) for describing suitable techniques and methodologies for production of recombinant gene constructs, production of transgenic animals incorporating such constructs and expression of the protein encoded in the mammary gland of the lactating adult female mammal. The disclosures of these references and the references recited above are incorporated herein by reference.

Reference is further made to Stacey et al in molecular and Cellular Biology 14(2): 1009–1016 (February 1994) which describes a knock-out experiment in which the mouse α-lactalbumin gene is replaced with a human α-lactalbumin gene. This paper (incorporated herein by reference) does not however report expression of the α-lactalbumin protein.

In one embodiment the present invention provides an expression system which has been produced by techniques other than by knock-out of the gene naturally present.

In a further aspect, the present invention provides a transgenic mammalian animal, said animal having cells incorporating a recombinant expression system adapted to express α-lactalbumin (preferably human α-lactalbumin) or a functional equivalent or part thereof. Generally the recombinant expression system will be integrated into the genome of the transgenic animal and will thus be heritable so that the offspring of such a transgenic animal may themselves contain the transgene and thus also be covered by the present invention. Suitable transgenic animals include (but are not limited to) sheep, pigs, cattle and goats. Cattle are especially preferred.

Additionally, the present invention comprises a vector containing such a recombinant expression system and host cells transformed with such a recombinant expression system (optionally in the form of a vector).

In a yet further aspect the present invention provides α-lactalbumin produced by expression of a recombinant expression system of the present invention, desirably such α-lactalbumin produced in a transgenic mammal. The α-lactalbumin gene is naturally activated in the mammary glands of the lactating female mammal. Thus the protein expressed by the recombinant expression system of the present invention would be produced at such a time and would be excreted as a milk component. It may also be possible for the protein of interest to be produced by inducing lactation through hormonal or other treatment. Processed milk products comprising such α-lactalbumin are also covered by the present invention.

In one preferred embodiment, the recombinant expression system comprises a construct designated pHA1, pHA2, pBBHA, pOBHA, pBAMA, p-Bova-A or pBova-B. The constructs pHA1, pHA2, pBBHA, pOBHA and pBAHA express human α-lactalbumin and are thus preferred, particularly pHA2.

Likewise transgenic mammals comprising the specific constructs listed above are preferred.

It has further been found that, in addition to increased concentrations of α-lactalbumin per unit volume of milk achieved by the present invention, where a human α-lactalbumin gene is present the volume of milk produced increases also. This finding is totally unexpected and for this reason constructs containing the human α-lactalbumin gene (or functional equivalents or parts thereof) and transgenic animals (especially cattle) are preferred embodiments of the invention.

Whilst we do not wish to be bound by theoretical considerations, it is further believed that the promoter region of the human α-lactalbumin gene is only partially responsible for the enhanced natural expression of α-lactalbumin by humans. It is believed that enhanced expression may be obtained by including within the recombinant expression system of the present invention the 3' sequence flanking the protein-encoding region and/or the 5' sequence flanking the protein-encoding region itself.

The flanking sequences 3' and 5' to the protein-encoding region of the human α-lac gene have been sequenced for the first time. These sequences are presented in SEQ ID Nos. 16 and 17 respectively. In experiments it has been observed that inclusion of either or both of these sequences give a surprisingly marked increase in expression levels of the α-lactalbumin protein. This increase in expression may be observed when the protein-encoding region is non-human α-lactalbumin as well as human α-lactalbumin.

Both the sequences of SEQ ID Nos. 16 and 17 are now believed to contribute towards the higher levels of expression of α-lactalbumin in human milk, and therefore comprise a further aspect of the present invention.

In a further aspect, the present invention provides a polynucleotide having a sequence substantially as set out in SEQ ID No. 16 or SEQ ID No. 17 or a portion or functional equivalent thereof.

The polynucleotides may be in any form (for example DNA or RNA, double or single stranded), but generally double stranded DNA is the most convenient. Likewise the polynucleotides according to the present invention may be present as part of a recombinant genetic construct, which itself may be included in a vector (for example an expression vector) or may be incorporated into a chromosome of a transgenic animal. Any vectors or transgenic animals comprising a polynucleotide as described above form a further aspect of the present invention.

Viewed from a yet further aspect the present invention provides a recombinant expression system (preferably adapted to express α-lactalbumin (preferably human α-lactalbumin) or a portion or functional equivalent thereof), said recombinant expression system comprising a polynucleotide selected from the polynucleotide located between the EcoRI and XhoI restriction sites of the wild-type α-lactalbumin gene and the polynucleotide located between the BamHI and EcoRI restriction sites of the wild-type human α-lactalbumin gene, or a portion or functional equivalents thereof.

In one preferred embodiment, the recombinant expression sequence of the present invention comprises both polynucleotides as defined above, portions and functional equivalents thereof.

The invention also encompasses vectors containing the recombinant expression systems defined above and cells transformed with such vectors. Further, the present invention comprises transgenic animals wherein the transgene contains the recombinant expression system.

BRIEF DESCRIPTION OF THE DRAWINGS

FIG. 1 as discussed in Example 1 and shows the sequence of bovine α-lactalbumin PCR primers.

SEQ ID No. 17 gives the sequence from the EcoRI restriction site to the XhoI restriction site which are 5' to the protein-encoding region of the endogenous human α-lactalbumin gene.

SEQ ID No. 16 gives the sequence from the BamHI to the vector restriction sites (including EcoRI sites) 3' of the protein-encoding region of the endogenous human α-lactalbumin gene.

Figure 9:
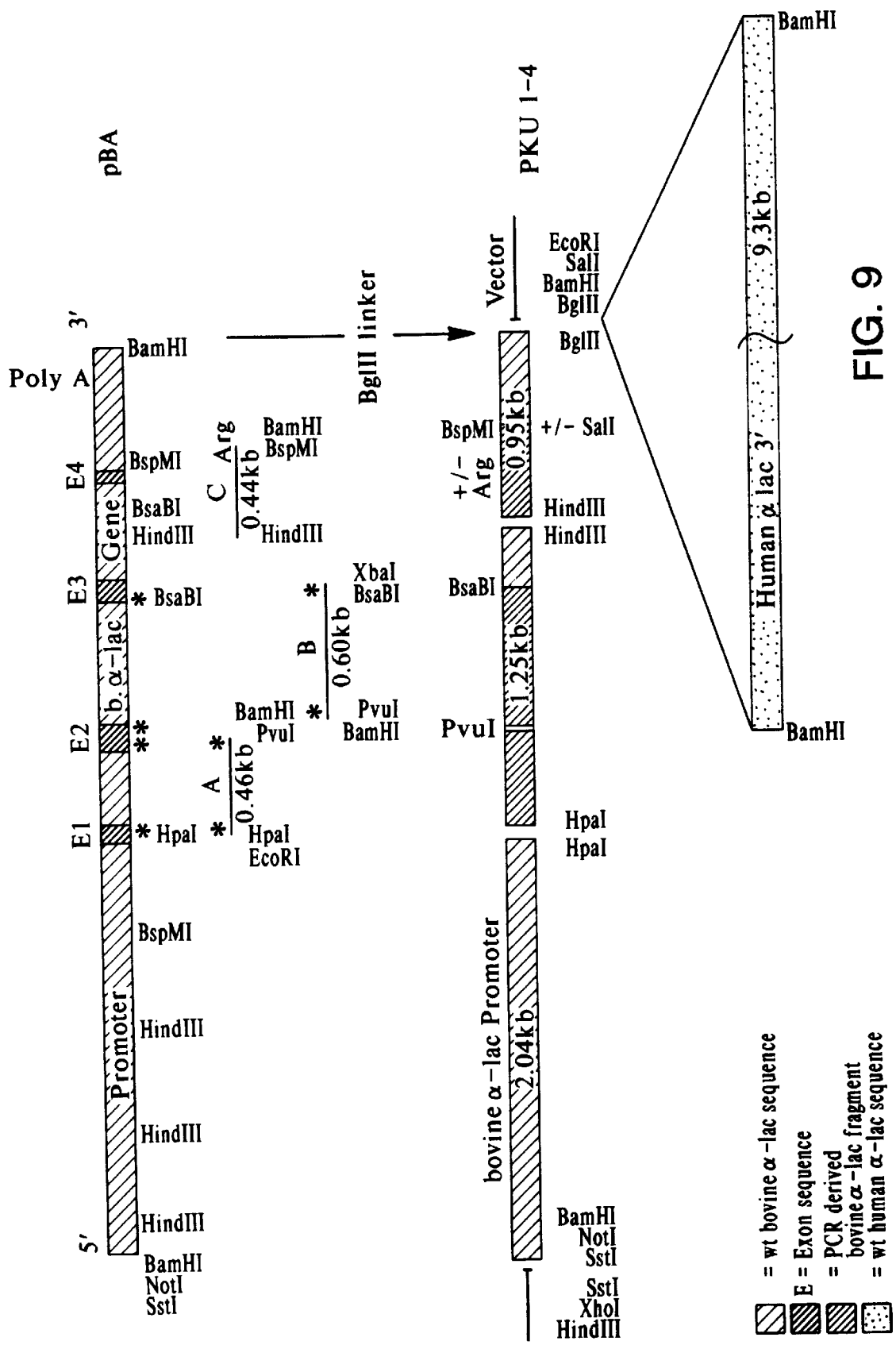

FIG. 9 shows the PCR cloning strategy for transgene constructs PKU1 to PKU4 as discussed in Example 6.

FIG. 10 gives the sequences of PKU primers 1 to 10 as discussed in Example 6.

Figure 11:
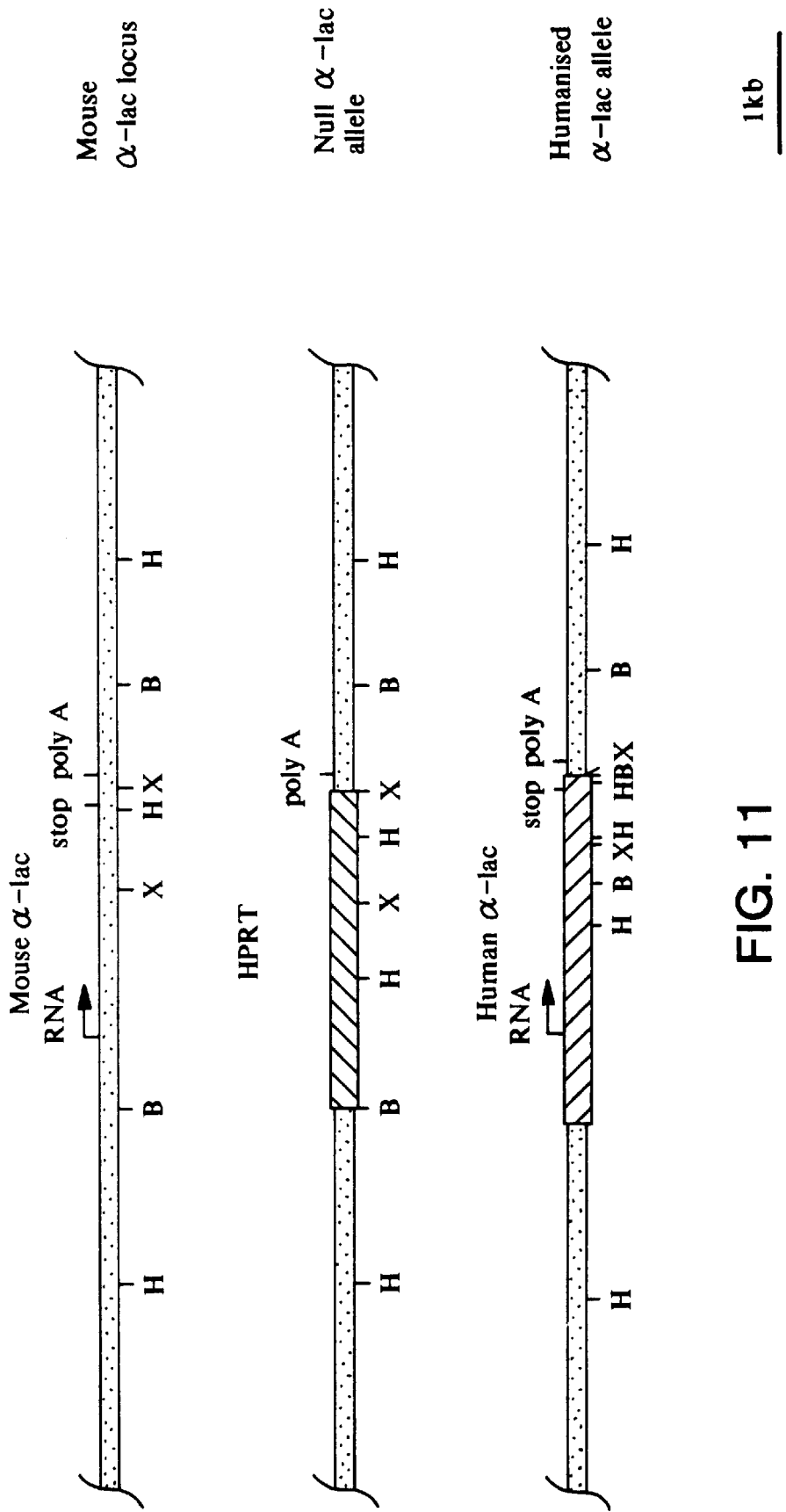

FIG. 11 shows the structure of null and humanised α-lactalbumin alleles.

Figures 12A, 12B:
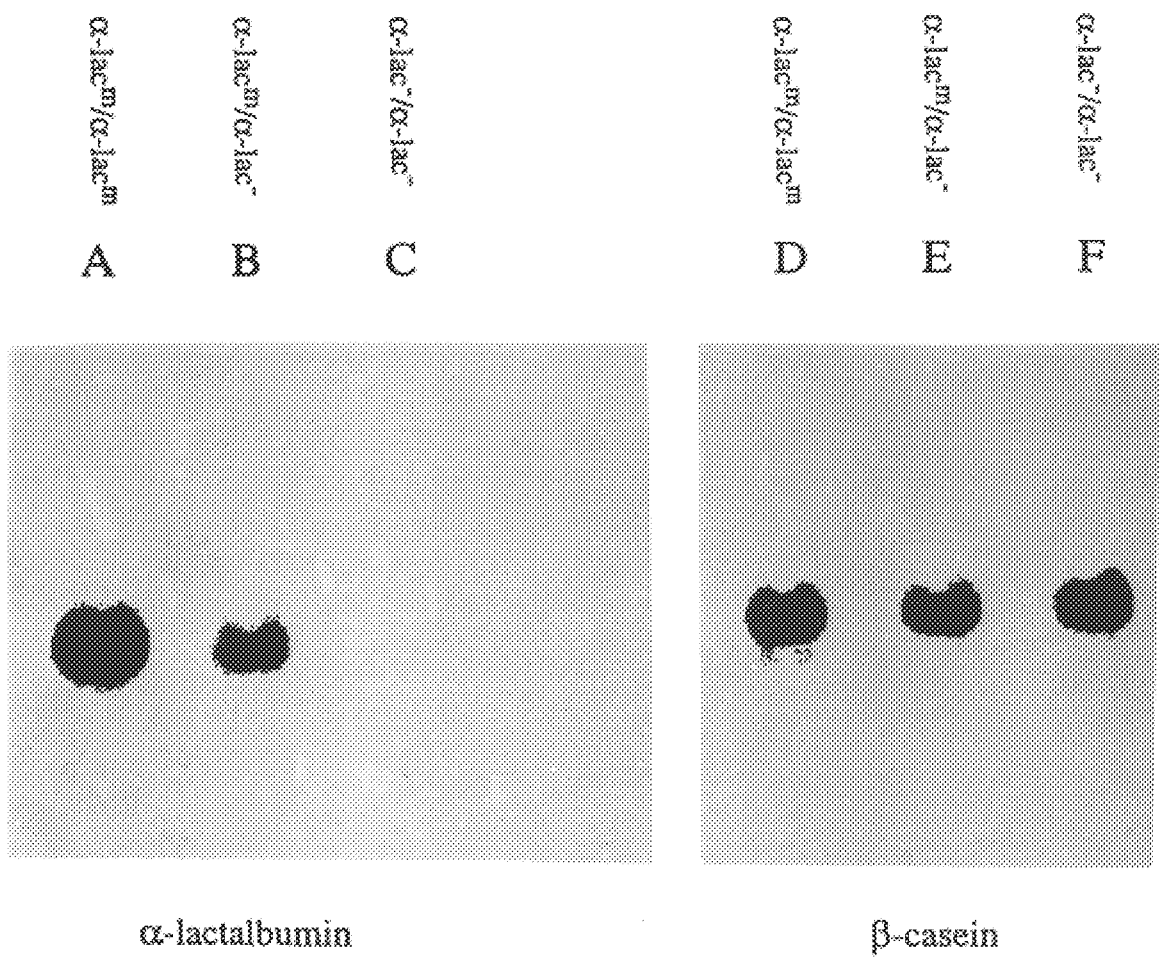

FIG. 12 is a Northern analysis of total RNA from α-lactalbumin-deficient lactating mammary glands.

Figure 13:
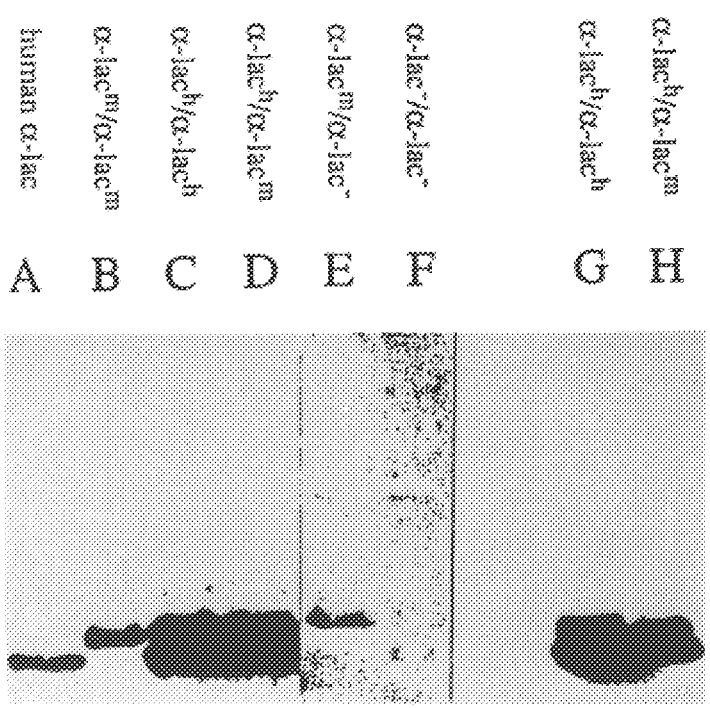

FIG. 13 illustrates a Western analysis of α-lactalbumin from targeted mouse strains.

Figure 14A:
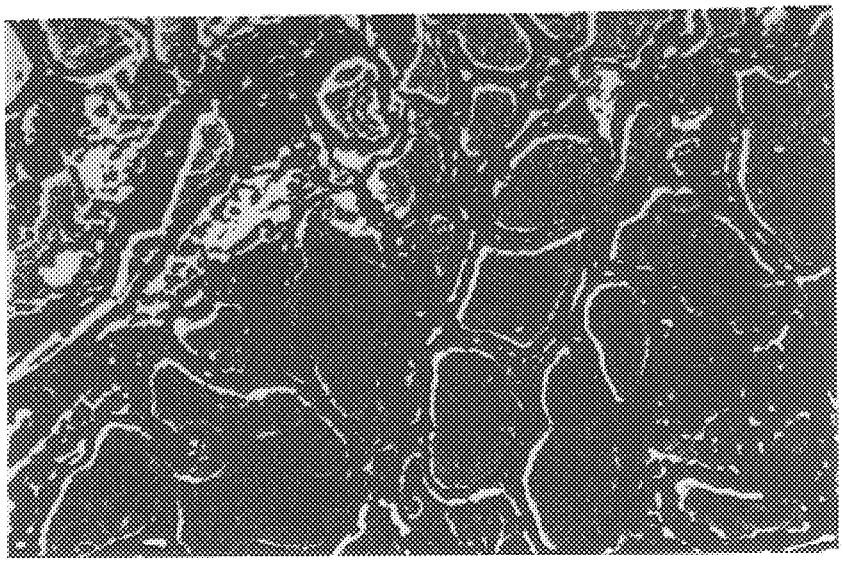
Figure 14B:
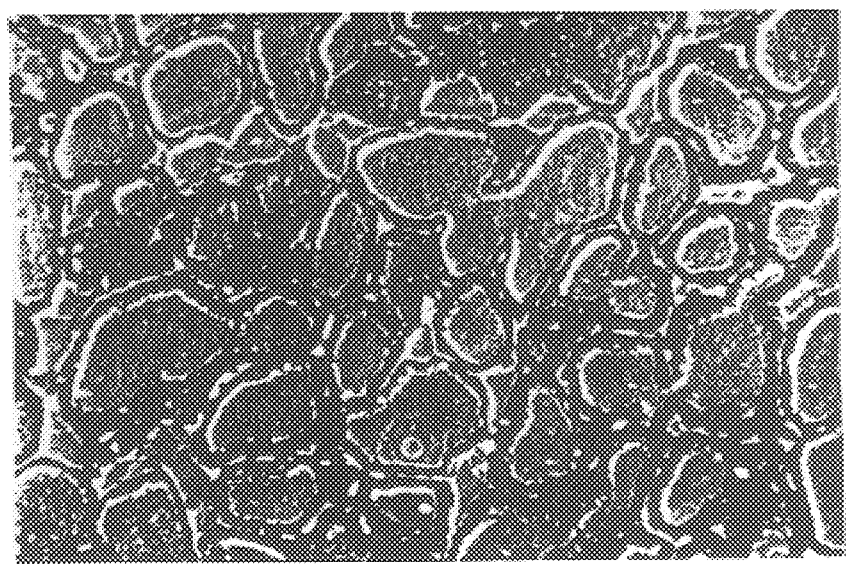
Figure 14C:
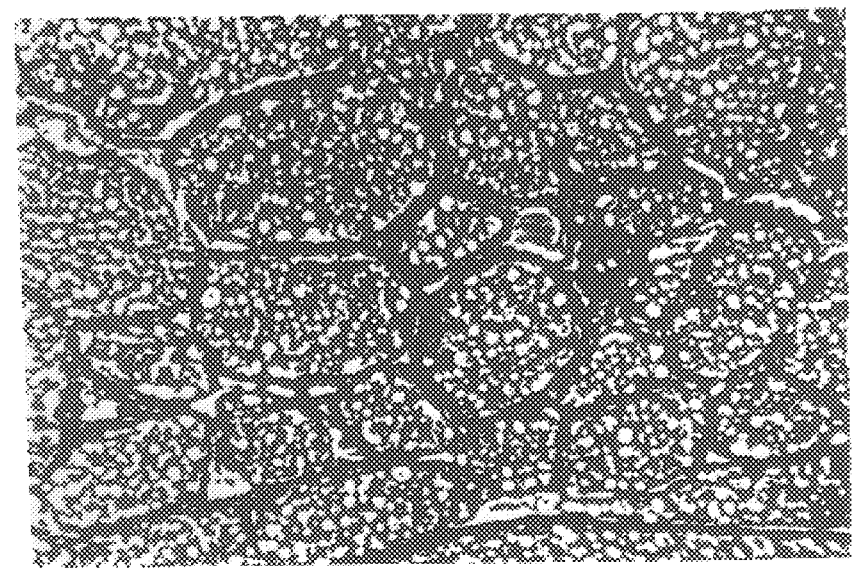

FIG. 14 (A–C) is a histological analysis of wild type and α-lac⁻ lactating mammary glands. FIG. 14A shows α-lac$^m$/α-lac$^m$ glands, FIG. 14B shows α-lac$^m$/α-lac⁻ glands, and FIG. 14C shows α-lac⁻/α-lac⁻ glands.

Figure 15A:
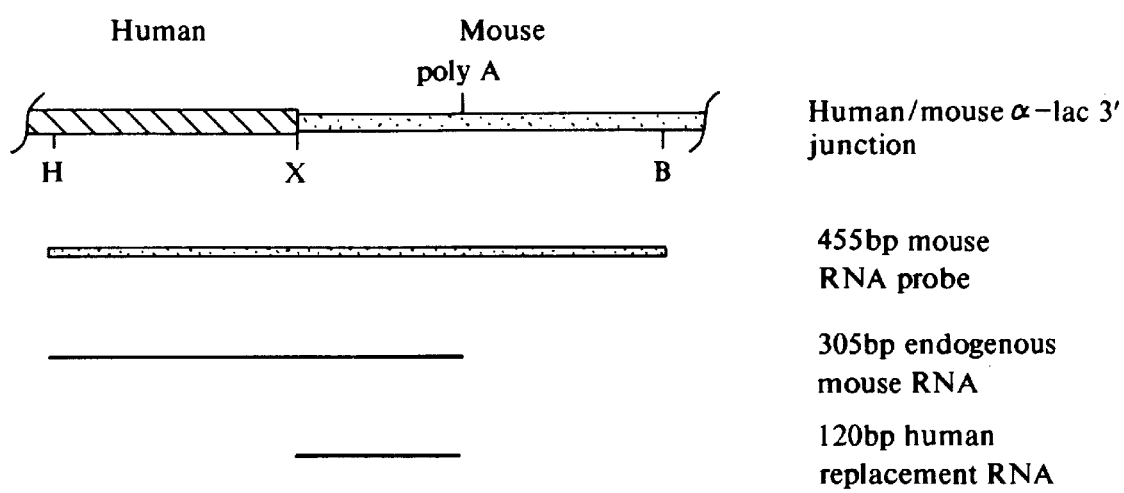
Figure 15B:
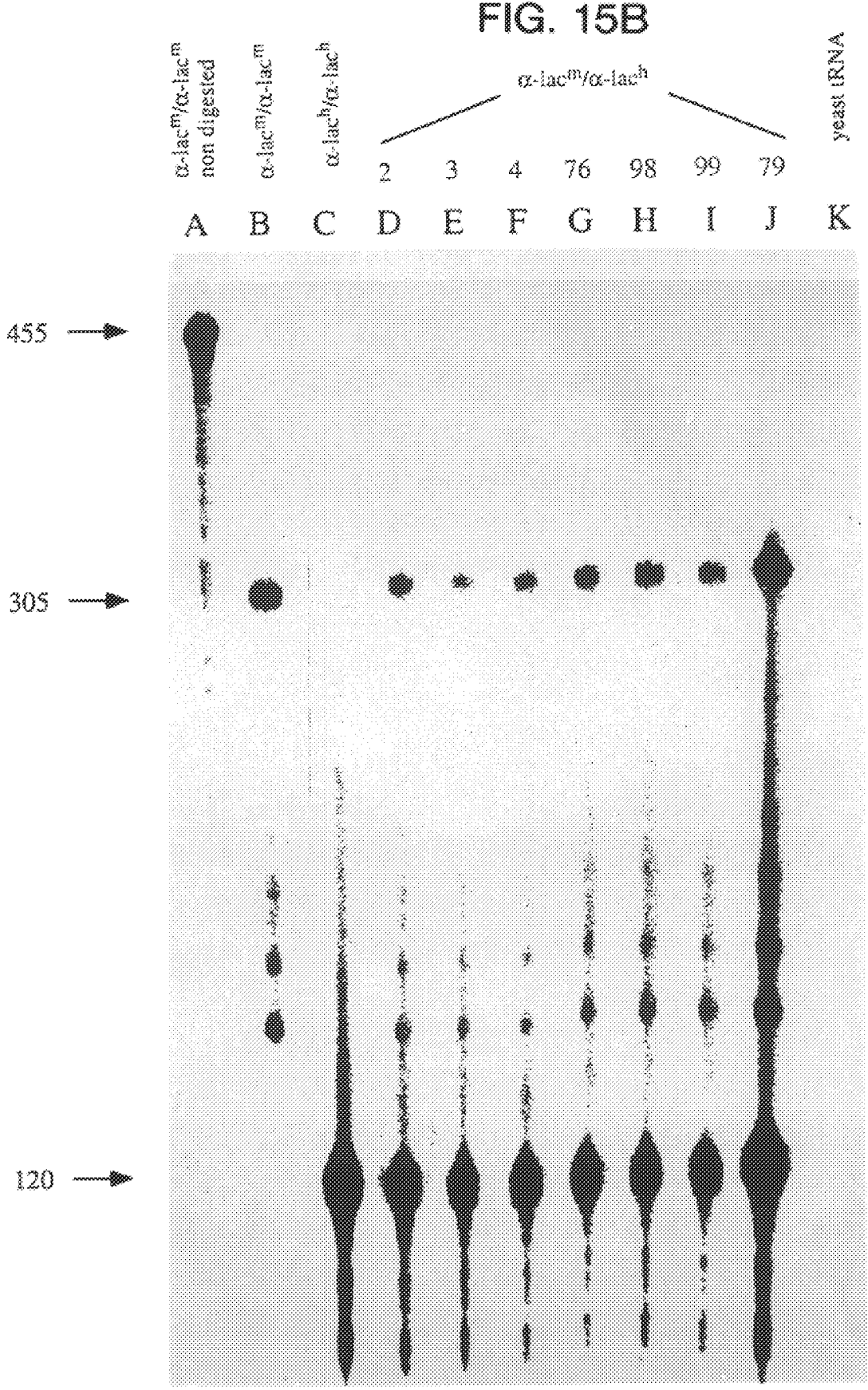

FIG. 15A shows an RNase protection assay used to distinguish human replacement and mouse α-lactalbumin mRNA and FIG. 15B shows an RNase protection assay of mouse and human replacement α-lactalbumin mRNA.

Figure 16A:
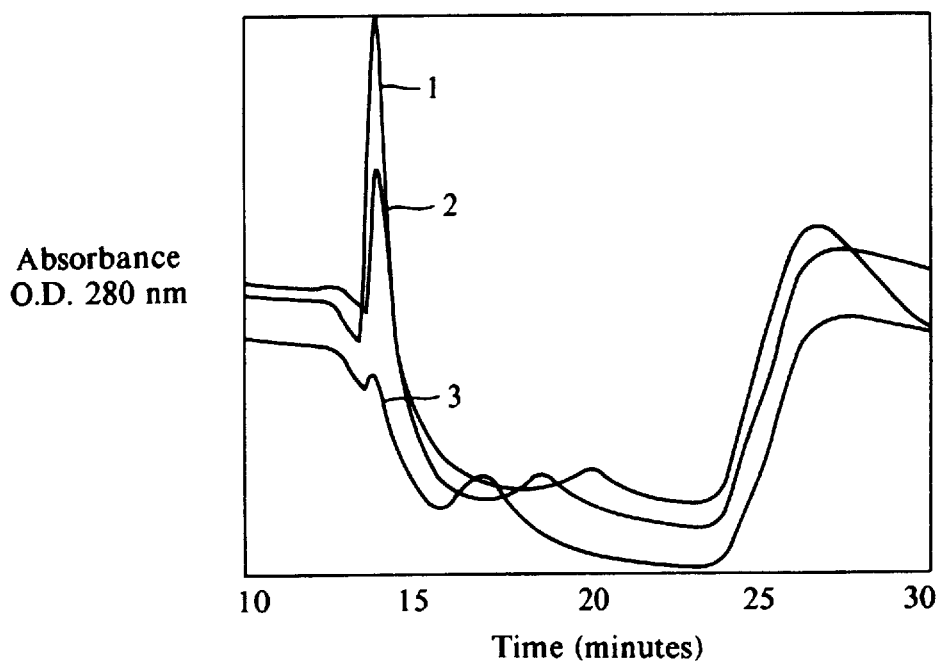
Figure 16B:
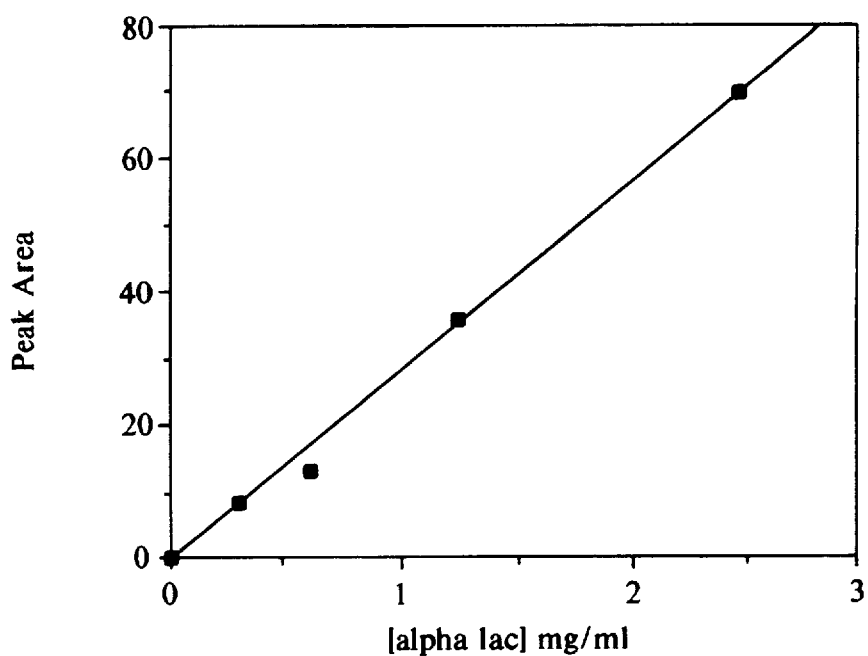

FIG. 16 gives the quantification of α-lactalbumin by hydrophobic interaction chromatography.

In more detail, in FIG. 11 the upper portion shows the wild type murine α-lactalbumin locus. The position and direction of the transcribed region is indicated by the arrow. The translational stop site and RNA polyadenylation sites are also indicated. The middle portion shows the structure of the null allele. The striped bar indictes the HPRT selectable cassette. The lower portion shows the structure of the human replacement allele. The checkered bar shows the human α-lactalbumin fragment. The transcription initiation, translational stop and polyadenylation sites are shown. Restriction enzyme sites shown are: HindIII (H); BamHI (B); XbaI (X).

In FIG. 12, the two autoradiographs shown are repeat hybridisations of the same membrane filter using a human α-lactalbumin probe followed by a rat β-casein probe. The probes used are indicated under each autoradiograph. The source of RNA in each lane is indicated above the lane markers.

In FIG. 13 Lane A contains purified human α-lactalbumin. Lanes B–F show samples of milk from targeted mice, genotypes are indicated above the lane markers. Lanes G and H are a shorter exposure of Lanes C and D.

The light micrographs shown in FIG. 14 are haemtoxylin/eosin stained sections of mammary tissue (original magnification 100×). The genotypes of each gland are indicated.

In FIG. 15A, the 3' junction between mouse and human DNA in the α-lac$^h$ allele lies between the translational stop site and the polyadenylation signal. Human α-lactalbumin mRNA contains 120 bp of mouse sequences in the 3' untranslated end. Human replacement and mouse α-lactalbumin mRNA were detected by hybridisation with a mouse RNA probe and distinguished by the size of RNA fragments protected from ribonuclease digestion. Human sequences are indicated by the chequered bar and mouse sequences by the shaded bar. Restriction enzyme sites shown are: HindIII (H); BaI (B); XbaI (X).

In FIG. 15B the autoradiograph shown is of a 5% polyacrylamide urea thin layer gel. The source of RNA is indicated above the lane markers. Lane A shows a wild-type RNA hybridised to the mouse RNA proe undigested with ribonuclease. Lanes D to J show RNA samples from α-lac$^m$/α-lac$^h$ heterozygotes, the numbers indicate individual mice and are the source of the quantitative estimates given in FIG. 15. The predicted size of protected fragments are indicated.

The upper portion of FIG. 16 shows phenyl-Sepharose elution profiles of three milk samples. 1, α-lac$^h$/α-lac$^h$ homozygote (mouse #22); 2, α-lac$^m$/α-lac$^h$ heterozygote (mouse #76); 3, α-lac$^m$/α-lac$^m$ wild type. The lower portion shows a standard curve of known quantities of human α-lactalbumin plotted against integrated peak area.

The present invention will now be further described with reference to the following, non-limiting, examples.

EXAMPLE 1

Cloning of Bovine α-lactalbumin gene

There are three known variants of bovine α-lactalbumin, of which the B form is the most common. The A variant from Bos (Bos) nomadicus f.d. indicus differs from the B variant at residue 10: Glu in A is substituted for Arg in B. The sequence difference for the C variant from Bos (Bibos) javanicus has not been established (McKenzie & White, Advances in Protein Chemistry 41, 173–315 (1991). The bovine α-lactalbumin gene (encoding the B form) was cloned from genomic DNA using the PCR primers indicated in FIG. 1. The primers have been given the following sequence ID Nos:

Ba-2 SEQ ID No 1
Ba-7 SEQ ID No 2
Ba-8 SEQ ID No 3
Ba-9 SEQ ID No 4

The source of DNA in all the PCR reactions was blood from a Holstein-Friesian cow.

The length of the amplified promoter region using primer Ba-9 in combination with primer Ba-8 is 0.72 kb. This BamHI/EcoRI fragment was cloned into Bluescript (pBA-P0.7).

The length of the amplified promoter region using primer Ba-7 in combination with primer Ba-8 is 2.05 kb. This BamHI/EcoRI fragment was cloned into Bluescript (pBA-P2).

The entire bovine α-lactalbumin gene including 0.72 kb of 5' and 0.3 kb of 3' flanking region was amplified using primer Ba-9 in combination with primer Ba-2. These primers include BamHI restriction enzyme recognition sites, which allowed direct subcloning of the amplified 3 kb fragment into the BamHI site of pUC18, giving rise to construct pBova-A (see FIG. 2).

Figure 2:
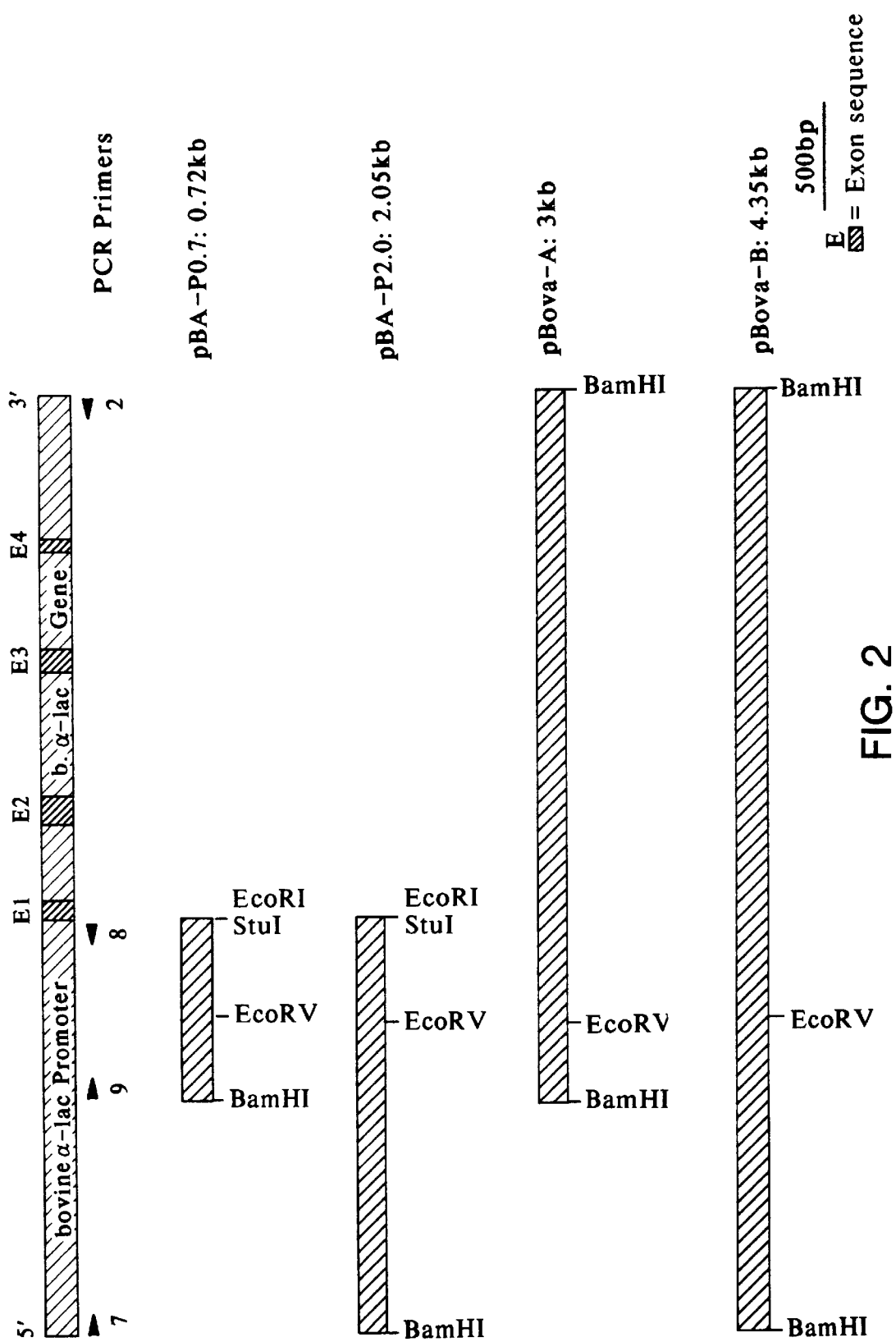
FIG. 2 is discussed in Example 1 and 4 shows the position of bovine α-lactalbumin PCR primers and products.

Ligation of the BamHI/EcoRV fragment from clone pBA-P2 to the EcoRV/BamHI fragment of pBOVA-a gave rise to construct pBOVA-b (see FIG. 2).

Since TAQ polymerase lacks proof-reading activity, it was essential to ensure that the amplified bovine α-lactalbumin DNA was identical to the published bovine α-lactalbumin gene. Sequence analysis was carried out across all the exons and the two promoter fragments. Comparison of the bovine α-lactalbumin exons with those published by Vilotte showed 3 changes:

(i) Exon I at +759 C to A. 5' non-coding region;
(ii) Exon I at +792 CTA to CTG. Both code for Leucine
(iii) Exon II at +1231 GCG to ACG. Alanine to Threonine This is indicative of the more common "B" form of the protein.

Although misreading of sequence during the PCR amplification cannot be ruled out, the above mismatches were probably due to the difference in the source of bovine DNA.

EXAMPLE 2

Cloning of Human α-Lactalbumin gene

Figure 3:
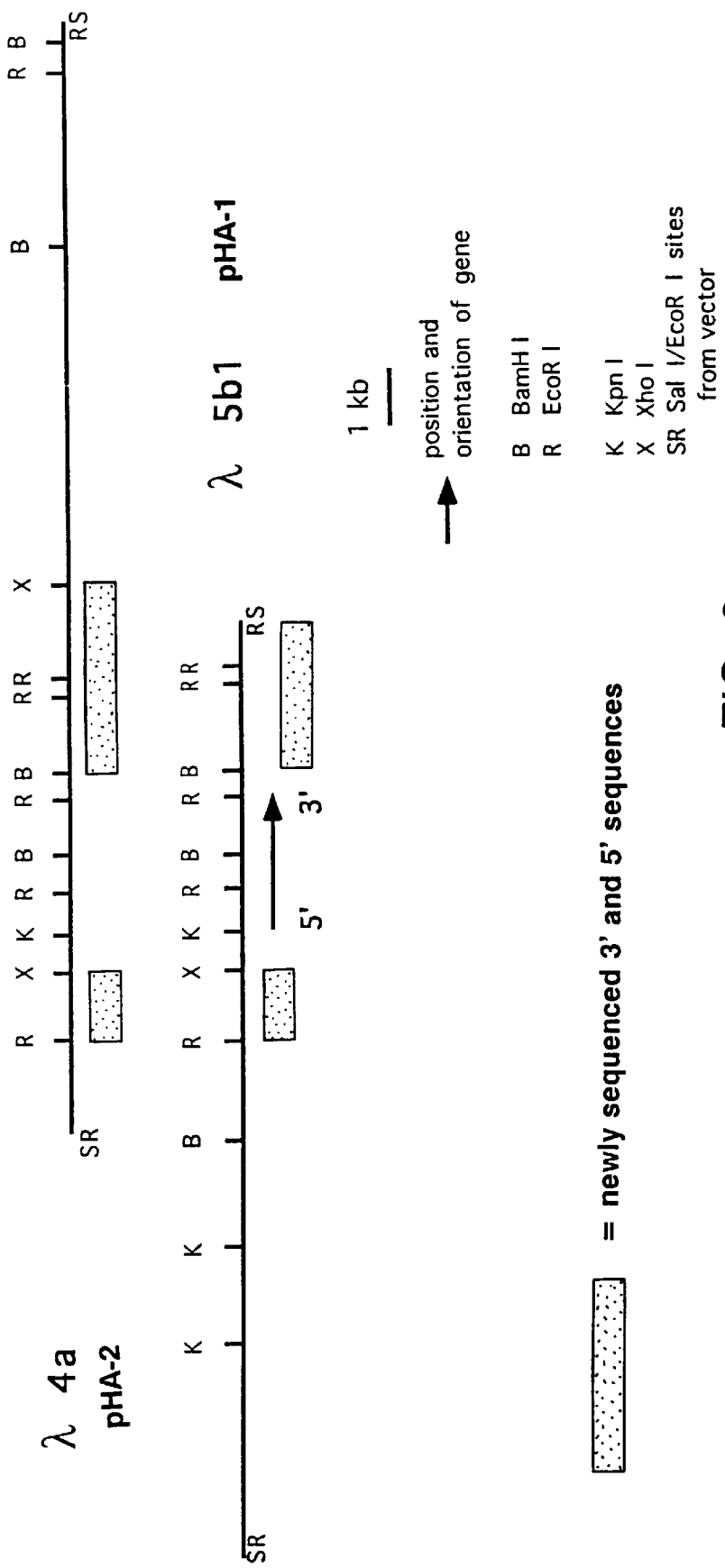
FIG. 3 is discussed in Example 2 and shows a restriction map of two overlapping genomic λ clones for the human α-lactalbumin gene (pHA-2 and pHA-1).

The DNA sequences of human α-lactalbumin has been published (Hall et al, Biochem. J., 242 735–742 (1987)). Using the human sequence, PCR primers were designed to clone two small fragments from human genomic DNA, one at the 5' end of the gene and the other at the 3' end. These were subcloned into the pUC18 vector and used as probes to screen a commercial (Stratagene) λ genomic library. Two recombinant bacteriophages, 4a and 5b.1, which contained the α-lactalbumin gene, were isolated by established methods (Sambrook et al, Molecular Cloning 2nd ed., Cold Spring Harbor Laboratory (1989)). Restriction mapping demonstrated that both clones contained the complete coding sequence for the human α-lac gene but differed in the amount of 5' and 3' sequences present. (FIG. 3). Sequence analysis of exons from clone 5b.1 and exons and 5' flanking region of clone 4a showed that these were identical to the published sequence.

The 3' sequence is given in SEQ ID No. 16 and the 5' sequence is given as SEQ ID No. 17.

EXAMPLE 3

Cloning of bovine beta lactoglobulin gene (bBLG)

Figure 4:
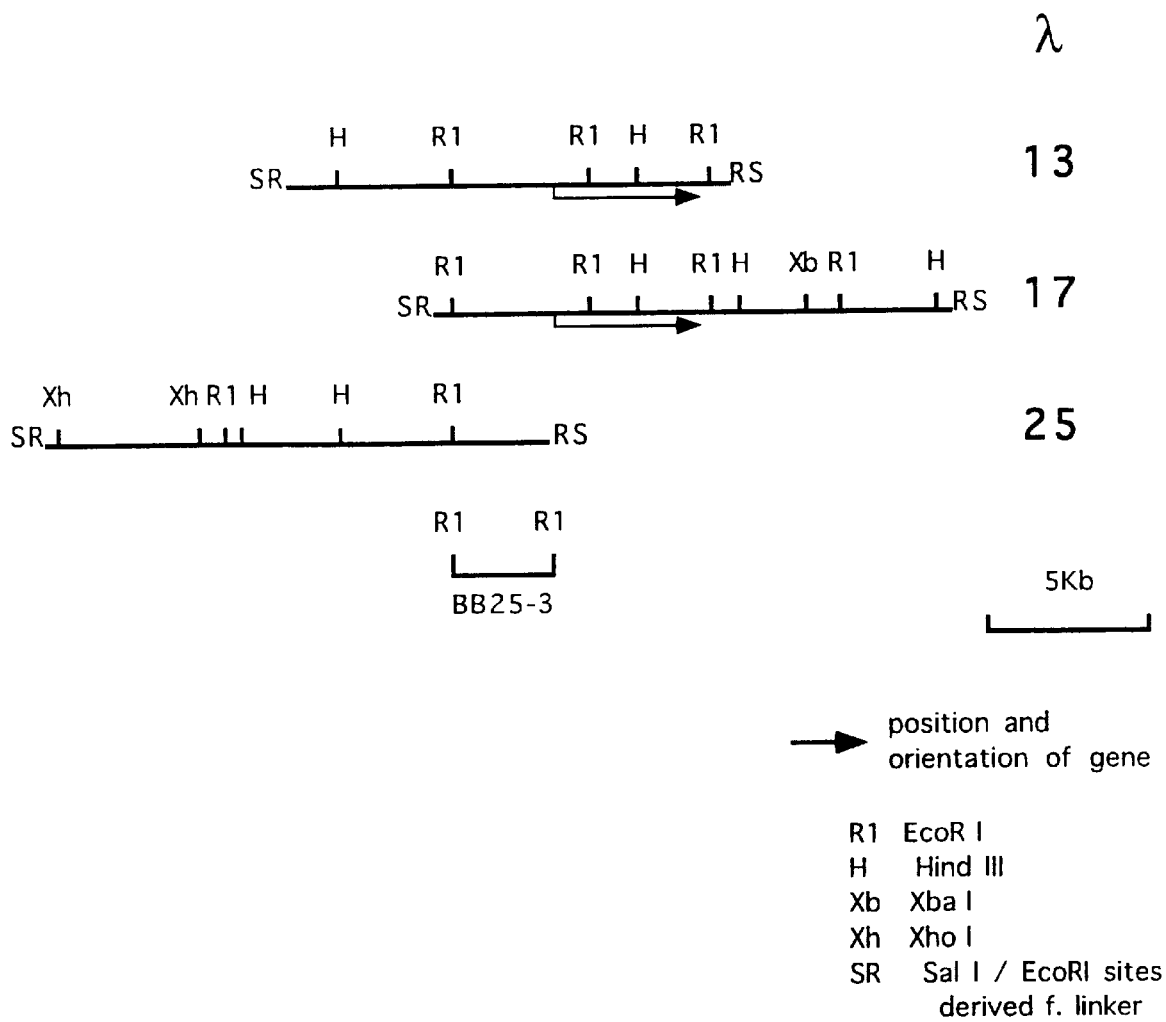
FIG. 4 is discussed in Example 3 and shows a restriction map of three overlapping genomic λ clones for the bovine beta-lactoglobulin gene.

The DNA sequence of bovine BLG (bBLG) has been published (Jamieson et al; Gene, 61; 85–90, (1987); Wagner, unpublished, EMBL Data Library: BTBLACEX (1991)). Using the bovine sequence, PCR primers were designed to clone a fragment from the 5' portion of the bovine BLG gene. This was subcloned into the pUC18 vector and used as probes to screen a commercial bovine (Stratagene) λ genomic library. Three genomic λ clones were isolated and characterised by restriction enzyme analysis (see FIG. 4). Two of the clones (BB13, BB17) contain the complete bBLC coding region plus various amounts of flanking regions, while clone BB25 lacks the coding region and consists entirely of 5' flanking region. Sequence analysis showed that the end of this clone lies 12 bp upstream of the ATG translation start site. SalI fragments containing the entire insert of clone BB13 and BB17 were subcloned into pUC18, as well as EcoRI fragments from clone BB25 (the latter was cloned into pBluescript (FIG. 4).

EXAMPLE 4

Assembly and expression of bovine α-lactalbumin constructs

Transgene constructs (FIG. 2)

pBova-A consists of the bovine α-lactalbumin coding region, ≅0.72 kb of 5' flank and 0.3 kb of 3' flank, cloned as a 3 kb BamHI fragment into Bluescript vector.

pBova-B consists of 3 fragments:
1. The 1.47 kb BamHI to EcoRV fragment from clone pBA-P2.
2. The 2.78 EcoRV to BamHI fragment from clone pBova-A.
3. The cloning vector Bluescript digested BamHI.

Bovine α-lactalbumin expression in transgenic mice

Figure 5:
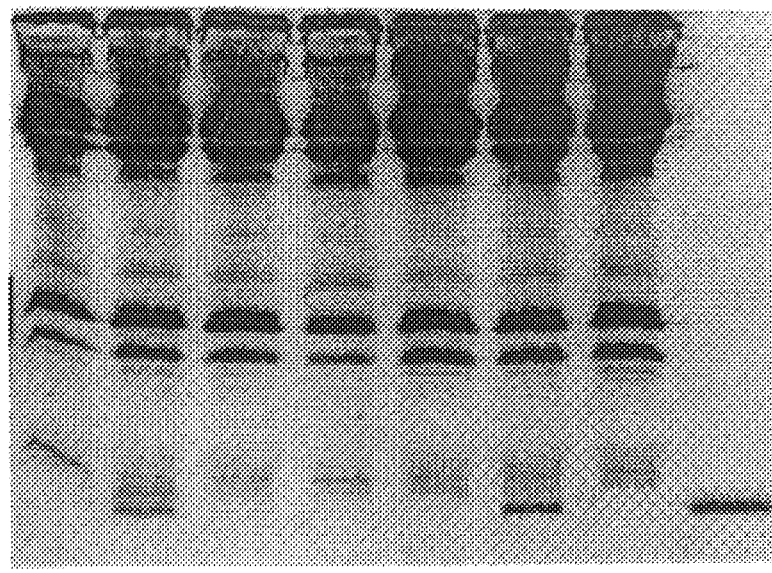
FIG. 5 is discussed in Example 4 and shows SDS-PAGE analysis of skimmed milk from bovine α-lactalbumin transgenic mice run against non transgenic mouse milk.

The two constructs pBova-A and pBova-B (FIG. 2) were injected into mouse embryos and gave rise to transgenic animals. Milk analysis by SDS-PAGE gel strained with Coomasie blue (referred to as "Coomassie gels") and comparison to standard amounts of α-lactalbumin showed expression levels of bovine α-lactalbumin varied from non detectable for pBova-A and up to ≅0.5–1 mg/ml for pBova-B (see FIG. 5 and Table 1).

TABLE 1

Bovine α-lactalbumin expression in transgenic mice

| Mouse | Coomassie |
| --- | --- |
| 244.12 BOVA-a | − |
| 244.14 BOVA-a | − |
| 244.15 BOVA-a | − |
| 245.23 BOVA-b | − |
| 245.8 BOVA-b | − |
| 245.4 BOVA-b | − |
| 245.7 BOVA-b | + |
| 245.21 BOVA-b | − |
| 245.13 BOVA-b | + |
| 249.13 BOVA-b | − |
| 246.15 BOVA-b | − |
| 249.18 BOVA-b | ++ |
| 249.23.1 BOVA-b | ++ |
| 249.23.5 BOVA-b | ++ |
| 249.25.3 BOVA-b | − |
| 249.25.7 BOVA-b | − |
| 249.30.3 BOVA-b | − |
| 249.30.4 BOVA-b | − |
| 249.33.2 BOVA-b | +/++ |
| 249.33.3 BOVA-b | +/++ |

− = <0.5 mg/ml
+ = ≅0.5–1 mg/ml
++ = ≅1–2 mg/ml

Table 1 shows the relative levels of bovine α-lactalbumin in transgenic mouse milk as estimated by comparison to protein standards on Coomassie gels.

EXAMPLE 5

Assembly and expression of human α-lactalbumin constructs

α-lactalbumin is the major whey protein in humans, beta-lactoglobulin the major whey protein in sheep and cow. The level of α-lactalbumin expression varies from species to species, human milk contains about 2.5 mg/ml, cow milk 0.5–1.0 mg/ml, and mouse milk 0.1–0.8 mg/ml. To define sequences which allow maximum expression of the human α-lactalbumin gene several different constructs were designed. These contain a) different amounts of 5' and 3' flanking regions derived from the human α-lactalbumin locus, b) 5' flanking regions derived from the bovine α-lactalbumin locus, or c) 5═ flanking regions derived from the bovine or ovine beta-lactoglobulin gene. The ovine beta-lactoglobulin gene promoter has been successfully used to allow high expression (>10 mg/ml) of heterologous genes in mouse milk.

Figure 6:
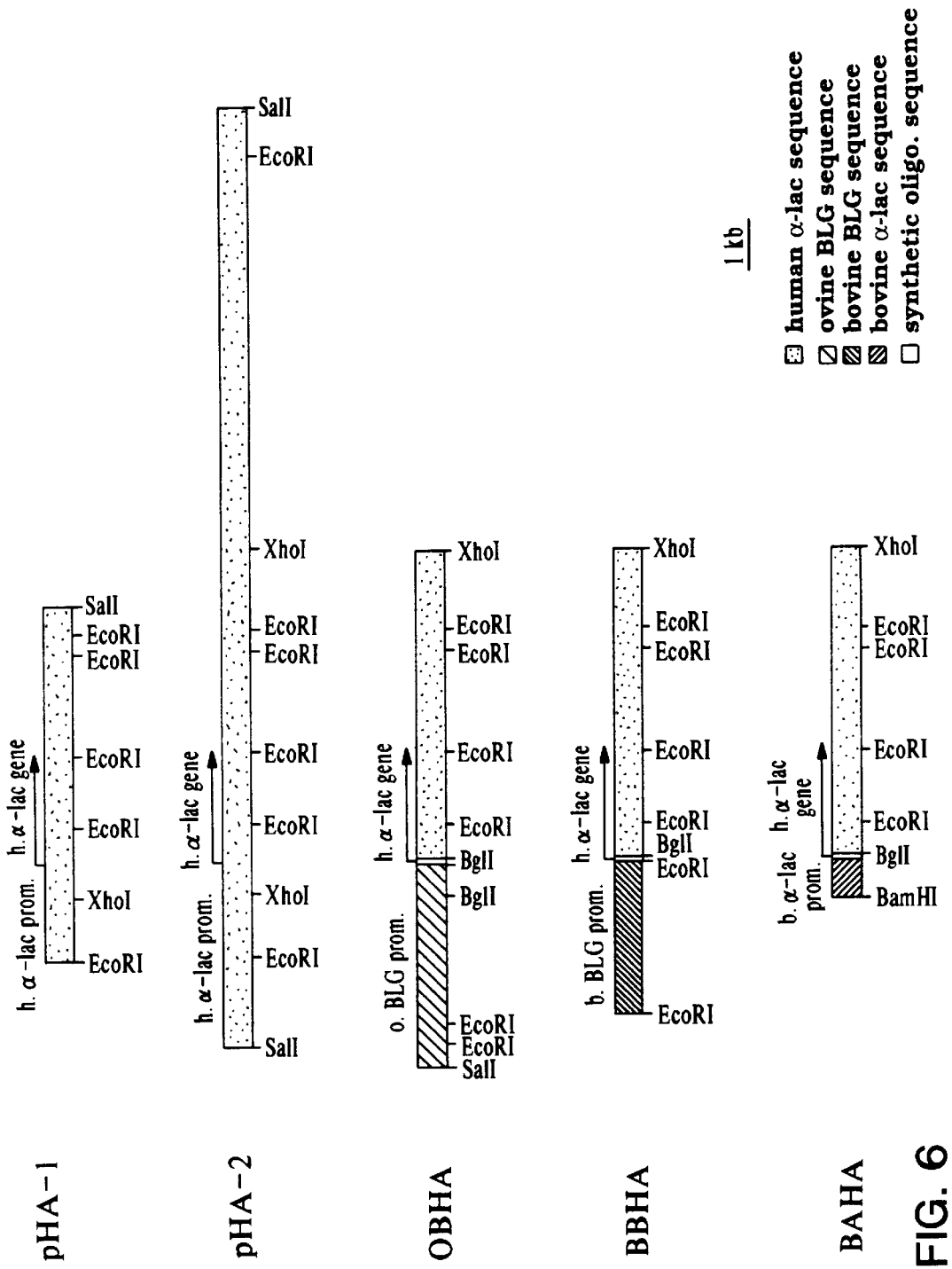
FIG. 6 is discussed in Example 5 and shows human α-lactalbumin transgene constructs.

Transgene constructs (FIG. 6)

pHA-1 consists of the human α-lactalbumin coding region, ≅1.8 kb of 5' flank and 3 kb of 3' flank derived from λ clone 5b.1 cloned as a 7 kb EcoRI/SalI fragment into puc18.

pHA-2 consists of the human α-lactalbumin coding region, ≅3.7 kb of 5' flank and ≅13 kb of 3' flank derived from λ clone 4a cloned as a ≅19 kb SalI fragment into puc18.

pOBHA (ovine beta-lactoglobulin, human α-lactalbumin) was constructed from 4 DNA fragments:
1. a 4.2 kb SalI/EcoRV fragment containing the ovine beta-lactoglobulin promoter (see WO-A-90/05188);
2. a 74 bp synthetic oligonucleotide corresponding to a 8 bp BclI linker and bases 15–77 of the human α-lactalbumin sequence used as a blunt/BglI fragment;
3. a 6.2 kb BglI/PstI human α-lactalbumin fragment derived from λ clone 4a comprising a region between a BglI site at base 77 and a XhoI site in the 3' flank;
4. pSL1180 (Pharmacia) cut with PstI and SalI.

pBBHA (bovine beta-lactoglobulin, human α-lactalbumin) was constructed from 4 DNA fragments:
1. a 3.0 kb EcoRI fragment containing the bovine beta-lactoglobulin promoter derived from clone BB25-3 and used as a EcoRI/EcoRV fragment;
2. a 74 bp synthetic oligonucleotide corresponding to a 8 bp BclI linker and bases 15–77 of the human α-lactalbumin sequence used as a blunt/BglI fragment;
3. a 6.2 kb BglI/PstI human α-lactalbumin fragment derived from λ clone 4a comprising a region between a BglI site at base 77 and a XhoI site in the 3' flank;
4. Bluescript vector cut with EcoRI and PstI.

pBAHA (bovine α-lactalbumin, human α-lactalbumin) was constructed from 4 DNA fragments:
1. a 0.72 kb BamHI to StuI fragment containing the bovine α-lactalbumin promoter derived from clone pBA-P0.7;
2. a 62 bp synthetic oligonucleotide corresponding to bases 15–77 of the human α-lactalbumin sequence used as a blunt/BglI fragment;
3. a 6.2 kb BglI/PstI human α-lactalbumin fragment derived from λ clone 4a comprising a region between a BglI site at base 77 and a XhoI site in the 3' flank;
4. Bluescript vector cut with BamHI and PstI.

Human α-lactalbumin expression in transgenic mice 5 constructs were injected into mouse embryos and gave rise to transgenic animals. All constructs expressed human α-lactalbumin in the milk of mice. pHA-1 and pHA-2, which contain the human α-lactalbumin gene and various amounts of flanking regions expressed between 1 to ≅18 mg/ml (213.5 pHA-2) in the majority of animals. pOBHA and pBBHA containing the human α-lactalbumin gene driven by either the ovine or bovine BLG promoter had slightly lower levels of expression. pBAHA containing the human α-lactalbumin gene driven by the 0.72 kb bovine α-lactalbumin promoter had expression levels similar to pHA-1 or pHA-2 but a lower percentage of transgenic animals expressed detectable levels of protein. This finding is surprising as the same bovine promoter sequence driving the bovine α-lactalbumin gene gave very poor results (see Example 4 and Vilotte et al; FEBS, Vol. 297, 1.2. 13–18 (1992)).

Table 2 gives a summary of the relative amount of the transgenic protein. Skimmed milk from these animals analysed by SDS-PAGE stained with Coomasie blue, isoelectric focusing, Western blots visualised with a commercial anti-human α-lactalbumin antibody (Sigma) and chromatofocusing. The results from these analyses showed that the transgenic protein was of the correct size, pI and antigenicity when compared to a human α-lactalbumin standard (Sigma).

TABLE 2

Human α-lactalbumin expression in transgenic mice

| Mouse | Coomassie | Western |
|---|---|---|
| 205.19 pHA1 | − | − |
| 204.10 pHA1 | ++ | ++ |
| 204.7 pHA1 | +++ | +++ |
| 230.15.3 pHA1 | +++ | n.d. |
| 230.15.5 pHA1 | +++ | n.d. |
| 230.15.6 pHA1 | +++ | n.d. |
| 230.21.5 pHA1 | +++ | n.d. |
| 230.21.1 pHA1 | ++ | n.d. |
| 211.18 pHA2 | + | ++ |
| 211.17 pHA2 | − | − |
| 211.16 pHA2 | +++ | +++ |
| 212.11 pHA2 | + | n.d. |
| 213.5 pHA2 | ++++ | ++++ |
| 212.13 pHA2 | ++ | n.d. |
| 212.19 pHA2 | − | n.d. |
| 213.4 pHA2 | +++ | n.d. |
| 212.7 pHA2 | − | n.d. |
| 232.10 BBHA | − | − |
| 233.1 BBHA | − | − |
| 231.4 BBHA | ++ | ++ |
| 232.9 BBHA | + | + |
| 231.9 BBHA | − | n.d. |
| 232.5 BBHA | + | + |
| 231.3 BBHA | + | + |
| 232.6 BBHA | − | n.d. |
| 237.6 BBHA | − | n.d. |
| 235.15 OBHA | − | n.d. |
| 235.19 OBHA | ++ | ++ |
| 236.6 OBHA | ++ | ++ |
| 234.1 OBHA | + | + |
| 234.4 OBHA | ++ | ++ |
| 234.14 OBHA | + | + |
| 239.14 BAHA | +++ | +++ |
| 239.4 BAHA | − | n.d. |
| 240.7 BAHA | − | n.d. |
| 239.3 BAHA | − | n.d. |
| 239.6 BAHA | ++ | ++ |
| 239.12 BAHA | − | n.d. |
| 243.1 BAHA | ++ | n.d. |
| 242.9 BAHA | +++ | n.d. |
| 241.16 BAHA | + | n.d. |
| 234.14 BAHA | − | n.d. |
| 243.13 BAHA | + | n.d. |
| 243.10 BAHA | − | n.d. |
| 243.4 BAHA | − | n.d. |

Figure 7A:
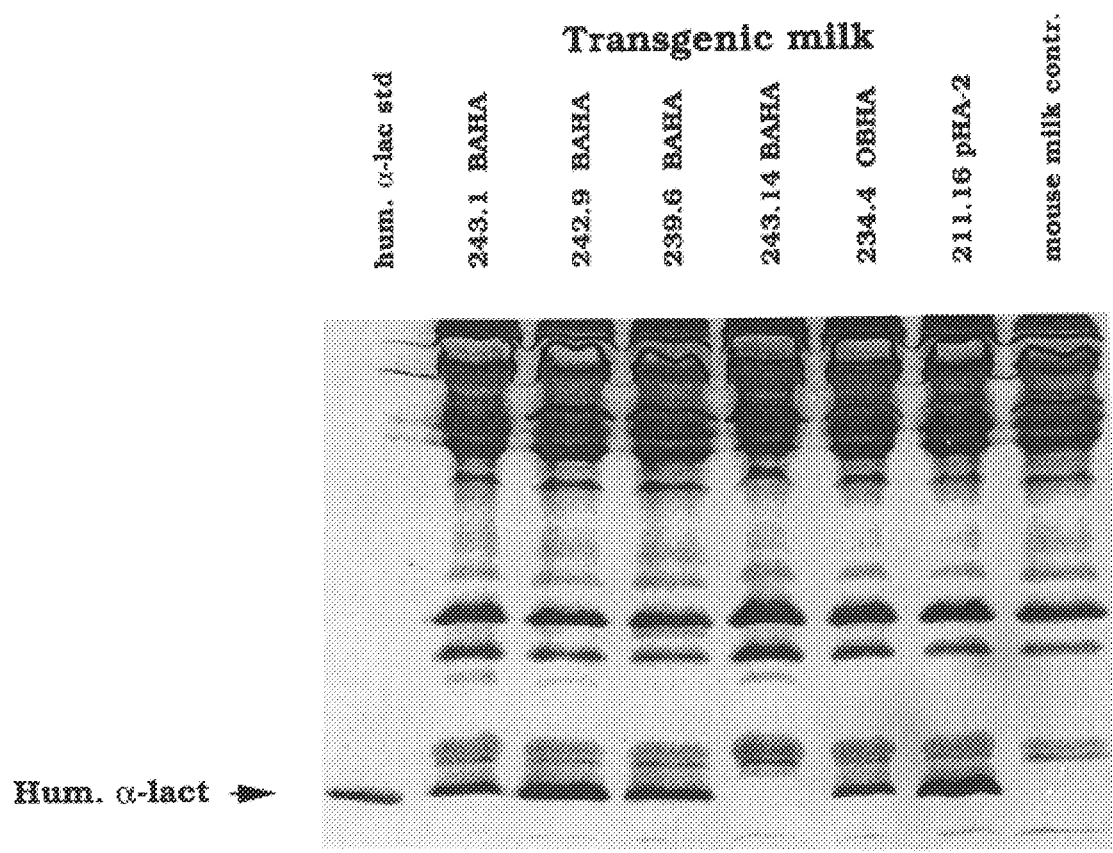
FIG. 7 (7A and 7B) is discussed in Example 5 and shows SDS-PAGE analysis of skimmed milk from human α-lactalbumin transgenic mice run against non transgenic mouse milk.
Figure 7B:
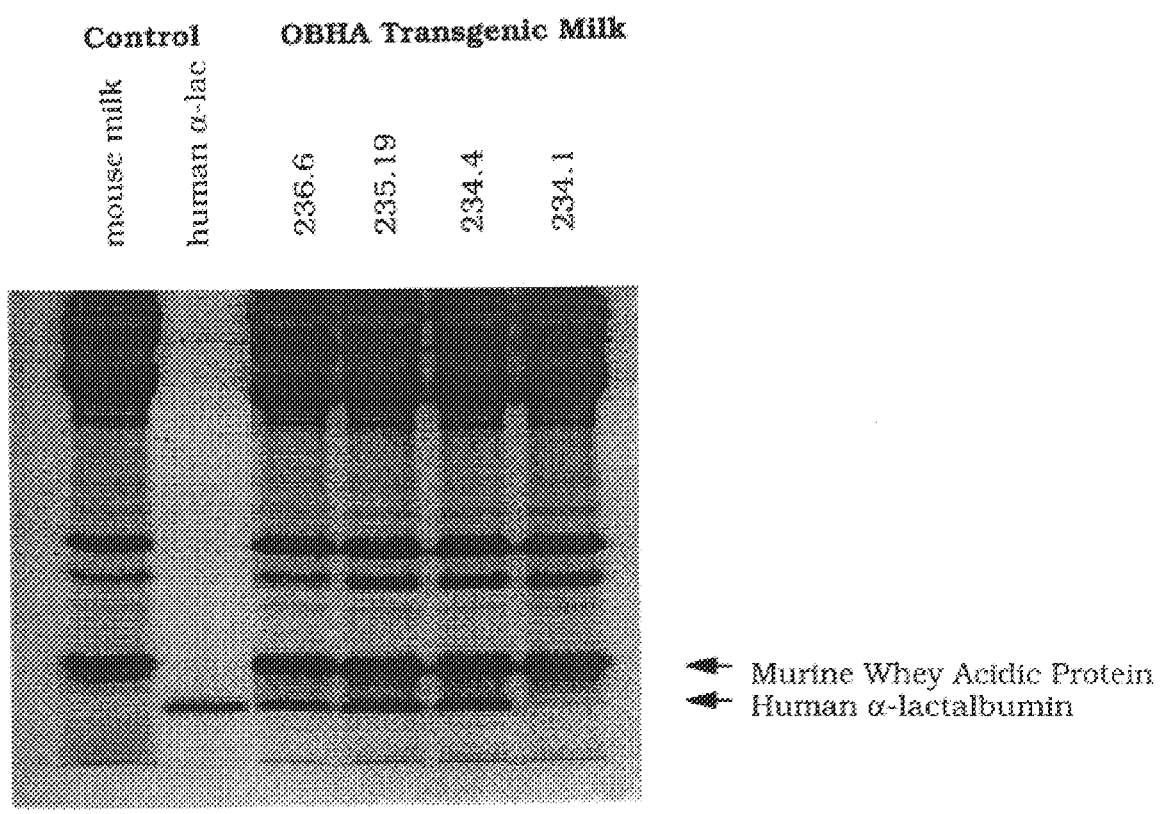
Figure 8:
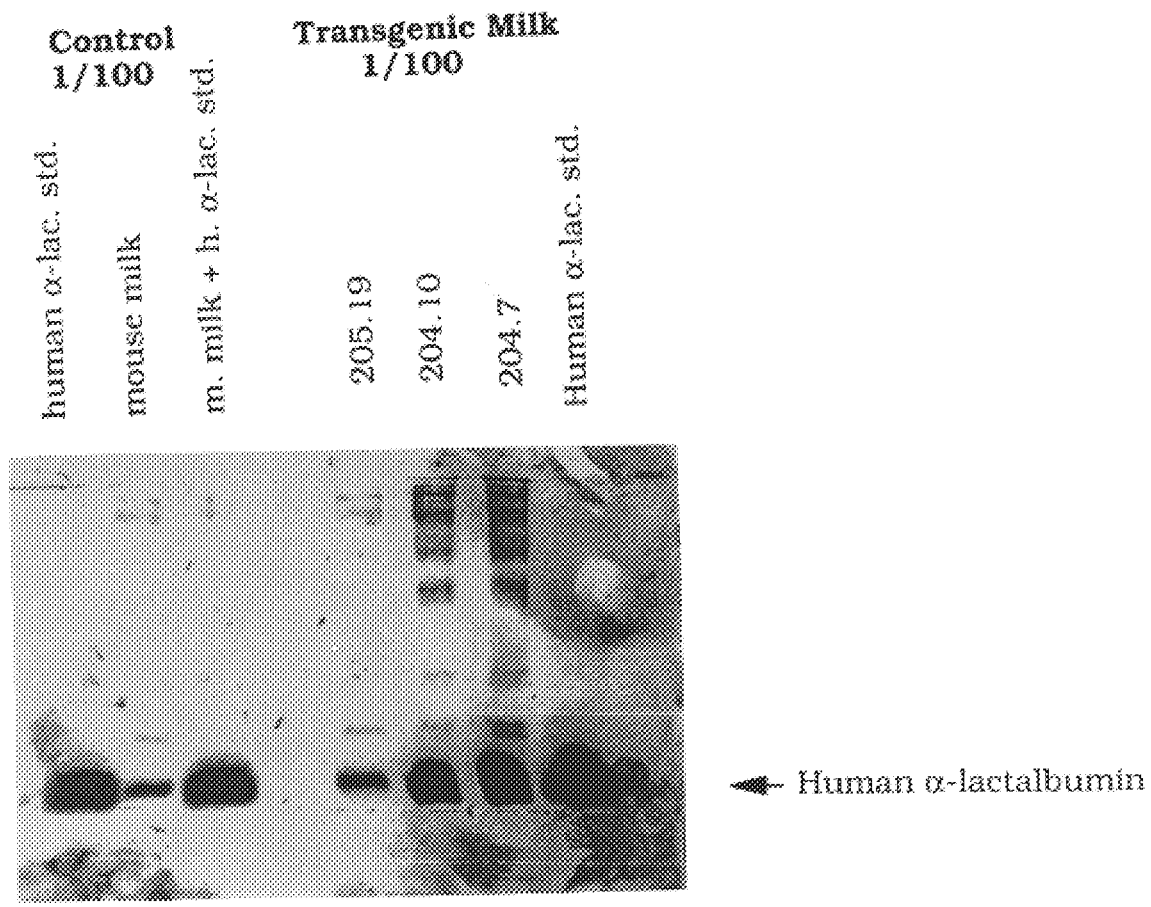
FIG. 8 is discussed in Example 5 and shows a Western analysis of the milk from human α-lactalbumin transgenic mice run against human α-lactalbumin standard.

Table 2 shows the relative levels of human α-lactalbumin in transgenic mouse milk as estimated by comparison to protein standards on Coomassie gels and Western Blots.
-=<0.5 mg/ml
+=≅0.5–1 mg/ml
++=≅1–2 mg/ml
+++=≅2–3 mg/ml
++++=>5 mg/ml
n.d.=not determined The results from several mice are shown in FIGS. 7 and 8. FIG. 7 shows an SDS-PAGE analysis of skimmed transgenic mouse milk run against a non-transgenic control mouse milk. FIG. 8 shows a Western blot of human α-lactalbumin transgenic milks run against a human α-lactalbumin standard.

EXAMPLE 6

Expression of Mutagenised Bovine α-Lactalbumin under the control of the Human α-Lactalbumin Promoter in vivo Expression of the human α-lactalbumin transgene is considerably higher than that of the native bovine α-lactalbumin transgene, reflecting the difference in expression levels of the endogenous bovine and human genes. As this might be caused by differences in the 5' control region, the 5' region of the bovine α-lactalbumin transcriptional start site was substituted with sequences from the human α-lactalbumin gene.

Two constructs were made, namely PKU-5 and PKU-1H, which incorporate the amino acid substitutions shown in Table 3.

The following SEQ ID Nos. have been assigned to the PCR primers used.

| | |
|---|---|
| PKU-1 | SEQ ID No. 5 |
| PKU-2 | SEQ ID No. 6 |
| PKU-2L | SEQ ID No. 7 |
| PKU-3 | SEQ ID No. 8 |
| PKU-4 | SEQ ID No. 9 |
| PKU-5 | SEQ ID No. 10 |
| PKU-6 | SEQ ID No. 11 |
| PKU-7 | SEQ ID No. 12 |
| PKU-8 | SEQ ID No. 13 |
| PKU-9 | SEQ ID No. 14 |
| PKU-10 | SEQ ID No. 15 |

PKU-5

In a first cloning step three fragments were subcloned into the EcoRI/BamHI site of pUC18:

(1) the EcoRI to PvuI fragment derived by PCR amplification using PKU-primer 7 in combination with 8 (see FIG. 10);

(2) the PvuI to BsaBI fragment derived by PCR amplification using PKU-primer 9 in combination with 10 (see FIG. 10); and (3) The BsaBI to HindIII fragment derived from pBA.

The final construct included 6 DNA fragments:

(1) the 3.7 kb SalI to KpnI fragment containing the human α-lactalbumin promoter derived from λ clone 4a (FIG. 3);

(2) the 152 bp synthetic oligonucleotide containing human α-lactalbumin sequences from the KpnI site to the AUG and bovine α-lactalbumin sequences from the AUG to the HapI site;

(3) the 1.25 kb HpaI to HindIII fragment from the first subcloning step;

(4) the 0.95 kb HindIII to BglII fragment derived from pBA;

(5) the 3.7 kb BamHI to XhoI fragment from the 3' flank of the human α-lactalbumin gene derived from λ clone 4a (FIG. 3) used as a BamHI fragment; and (6) a Bluescript KS- vector cut with SalI and BamHI.

PKU-1H was constructed in the same way as PKU-5 with the exception of fragment (3), which was derived from PKU 1.

PKU-1 was constructed from six DNA fragments (see FIG. 9):

(1) a 2.04 kb SstI to HpaI fragment derived from pBOVA-6;

(2) a 0.46 kb HpaI to PvuI fragment derived from PCR product A (PKU-primer pair 1 and 2; see FIG. 10);

(3) a 0.60 kb PvuI to BsaBI fragment derived from PCR product B (primer pair 3 and 4; see FIG. 10);

(4) a 0.22 kb BsaBI to HindIII fragment derived from pBOVA-6;

(5) a 0.95 kb HindIII to BglII fragment derived from pBOVA-6;

(6) the vector pSL1180 digested with SstI and BglII.

TABLE 3

Amino Acid Substitutions present in Transgene Constructs

| | Substitutions | | | | Human promoter Human 3' flank | Plasmid |
|---|---|---|---|---|---|---|
| pos'n | 9 | 31 | 53 | 80 | | |
| | Tyr, | Tyr, | Tyr, | Tyr | + | pPKU-1H |
| | Ser, | Tyr, | Leu, | Leu | + | pPKU-5 |

Expression in transgenic mice

The two constructs PKU-1H and PKU-5 have been injected into mouse embryos. So far transgenic animals were derived for the PKU-5 construct. These animals are set up for breeding to allow milk analysis.

EXAMPLE 7

Effect on Lactation by disruption of α-Lactalbumin deficiency and insertion of human α-Lactalbumin gene replacement in mice Materials and Methods Mouse lines Mice carrying the null α-lactalbumin allele and the humanised α-lactalbumin replacement allele were derived by breeding chimeras produced from the targeted embryonic stem cell clones M2 and F6 respectively against Balb/c mates, as described previously (Fitzgerald et al J. Biol. Chem 245:2103–2108). During the breeding of these strains, α-lactalbumin genotypes were determined by Southern analysis of genomic DNA prepared from tail biopsies.

RNA analysis

Total RNA was prepared by the method of Auffray and Rougeon (Eur. J. Biochem 107:303–14) from abdominal mammary glands of female mice 506 days postpartum. Northern analysis was carried out according to standard procedures (Sambrook et al, Molecular cloning). Probes used for hybridisation were: a 3.5 kb BamHI fragment containing the complete mouse α-lactalbumin gene; and a 1.1 kb rat β-casein cDNA (Blackburn et al Nucl. Acids Res 10:2295–2307).

RNAse protection analysis $^{32}$P-CTP radiolabelled antisense RNA was transcribed by T7 RNA polymerase (Promega) from a 455 bp HindIII-BalI mouse α-lactalbumin fragment (FIG. 15A) cloned in Bluescript KS. The conditions for the transcription reaction, solution hybridisation and RNAse digestion were as recommended by Promega. Protected fragments were separated by polyacrylamide gel electrophoresis and visualised by autoradiography.

Milk composition and yield analysis

Milk samples were collected between days 3–7 of lactation under Hypnorm (Roche)/Hypnovel (Janssen) anaesthesia. 150 mU of oxytocin (Intervet) was administered by intraperitoneal injection and milk expelled by gentle massage. Milk fat content was measured as described by Fleet and Linzell (J. Physiol 175:15). Defatted milk was assayed for protein (Bradford Analyt. Biochem 72:248–54) and lactose was measured enzymatically by sequential incubation with β-galactosidase, (Boehringer) glucose oxidase and peroxidase (Sigma) by a method adapted from that of Bergmeyer and Bernt (Methods in Enzyme Analysis 3:1205–1212).

Milk yield was estimated using a titrated water technique described by Knight et al., (Comp. Biochem. Physiol 84A:127–133) in mice suckling young over a 48 hour period between days 3 and 6 of lactation.

Milk α-lactalbumin analysis and quantification

Milk samples were analysed on 16% of SDS-PAGE gels (Novex) and western blotted onto Immobilon P membrane. α-lactalbumin was detected by absorption with rabbit anti-human α-lactalbumin antiserum (Dako), followed by goat anti-rabbit IgG peroxidase antibody conjugate and visualised with an enhanced chemiluminescence system (Amersham).

α-lactalbumin in milk samples was quantified by a modification of the method of Lindahl et al., (Analyt. Biochem 140:394–402) for calcium dependant purification of α-lactalbumin by phenyl-Sepharose chromatography. Milk samples were diluted 1:10 with 27% w/v ammonium sulphate solution, incubated at room temperature for 10 minutes and centrifuged. Supernatant was mixed with an equal volume of 100 mM Tris/Cl, pH 7.5, 70 mM EDTA and loaded onto a column (200 μl packed volume) of phenyl-Sepharose (Pharmacia) pre-equilibrated with 50 mM Tris/Cl, pH 7.5, 1 mM EDTA. The column was washed with the same buffer and α-lactalbumin eluted with 50 mM Tris/Cl, pH 7.5, 1 mM $CaCl_2$. The optical absorbance at 280 nm of the column was monitored and integrated peak areas corresponding to the α-lactalbumin fraction computed. A standard curve was constructed using known quantities of purified human α-lactalbumin from 0 to 2.46 mg/ml (FIG. 16).

Histology

Pups were removed for two hours from lactating mothers on the sixth day postpartum, mothers sacrificed and thoracic mammary glands were dissected, preserved in neutral buffered formalin, paraffin embedded and stained with haematoxylin/eosin by standard methods.

Results

Mouse α-lactalbumin gene deletion

A line of mice in which a 2.7 kb fragment covering the complete mouse α-lactalbumin coding region and a 0.57 kb of promoter has been deleted and replaced with a 2.7 kb fragment containing a hypoxanthine phosphoribosyltransferase (HRPT) selectable marker gene was established as described in Stacey et al, 1994 supra (see FIG. 11). Animals carrying this allele are designated α-lac-. The wild type mouse α-lactalbumin allele is designated α-lac$^m$.

Northern analysis of RNA from mammary glands taken on the fifth day of lactation showed that α lactalbumin mRNA was absent in α-lac-/α-lac- homozygotes (see FIG. 12) confirming that the targeted α-lactalbumin gene has been removed and that no other source of α-lactalbumin mRNA exists. Hybridisation of the same RNA samples with a β-casein RNA in all samples (see FIG. 12). α-Lactalbumin deficiency has no apparent effect in mice other than during lactation. α-lac-/α-lac- homozygotes and α-lac$^m$/α-lac-heterozygotes of both sexes are normal in appearance, behaviour and fertility. However, α-lac-/α-lac- homozygous females cannot rear litters successfully. Their pups fail to thrive and die within the first 5–10 days of life. Offspring of homozygous α-lac-/α-lac- females do survive normally when transferred to wild type foster mothers. Conversely, offspring from wild type mothers transferred to homozygous α-lac-/α-lac- mothers are not sustained. Table 4 shows that pups raised by α-lac-/α-lac- mothers are approximately half the weight of those raised by α-lac$^m$/α-lac$^m$ wild type mice. Estimates of milk yield are consistent with this, α-lac$^m$/α-lac- heterozygotes produce similar quantities of milk as wild type, but the yield of α-lac-/α-lac- homozygotes was severely reduced (Table 4).

TABLE 4

Milk composition, pup weight, mammary tissue weight and milk yield in targeted mouse lines

| Geneotype | α-lac$^m$/α-lac$^m$ | α-lac$^m$/α-lac- | α-lac-/α-lac- | α-lac$^m$/α-lac$^h$ | α-lac$^h$/α-lac$^h$ |
|---|---|---|---|---|---|
| Fat (% v/v) | 28.23 ± 1.65(7) | 29.6 ± 1.3(6) | 45.25 ± 2.15(6)*** | 25.25 ± 1.36(7) | 21.2 ± 0.23(4)* |
| Protein (mg/ml) | 87.52 ± 5.82(7) | 95.81 ± 9.5(5) | 164.63 ± 13.92(8)*** | 94.51 ± 5.97(7) | 77.07 ± 1.05(4) |
| Lactose (mM) | 62.44 ± 9.27(7) | 42.7 ± 4.2(6) | 0.7 ± 0.34(3)*** | 42.40 ± 1.93(7) | 56.85 ± 3.8(4) |
| Single pup weight (g) | 2.82 ± 0.25(8) | 3.14 ± 0.1(7) | 1.52 ± 0.12(10)*** | 2.9 ± 0.15(8) | 3.4 ± 0.75(4) |
| Mammary tissue weight per pup (g) | 0.34 ± 0.06(7) | 0.4 ± 0.1(7) | 0.35 ± 0.05(8) | 0.31 ± 0.04(6) | 0.51 ± 0.09(4) |
| Milk yield (g/day) | 7.51 ± 0.44(4) | 6.7 ± 0.38(6) | 1.37 ± 0.48(4)*** | n.t. | 9.94 ± 0.65(5)* |

Statistical analysis by unpaired t-test, *p < 0.05; p < 0.01; *p < 0.001;
Values are mean ± SE.
Figures in brackets indicate the number of mothers analysed.
n.t., not tested Milk was obtained from each genotype by manual milking and the composition of key components analysed. Milk from α-lac$^m$/α-lac-heterozygotes was indistinguishable in appearance from wild type milk and showed fat and protein contents similar to wild type (Table 4). While lactose concentration appeared to be slightly reduced in α-lac$^m$/α-lac- heterozygotes, statistical analysis showed that the difference was not significant. In contrast, milk from α-lac-/α-lac- homozygotes was viscous, difficult to express from the teats and was markedly different in composition to wild type. Fat content was ~60% greater than wild type, protein content was ~88% greater, and lactose was effectively absent. The apparent 0.7 mM lactose detected in α-lac-/α-lac- females represents milk glucose content, since the lactose assay used involved the enzymatic conversion of lactose to glucose. Direct assay of glucose in wild type milk indicated a concentration of 1.8 mM.

Western analysis of milk protein failed to detect α-lactalbumin in milk from α-lac-/α-lac- homozygotes (see FIG. 13, Lane F). This was confirmed by phenyl-Sepharose chromatography, a technique used to specifically identify α-lactalbumin which has been adapted to obtain quantitative estimates of milk α-lactalbumin content (Table 5; see also FIG. 16). When applied to milk from α-lac-/α-lac- homozygotes no α-lactalbumin was detected. In contrast, α-lactalbumin concentration in α-lac$^m$/α-lac- heterozygote milk was estimated as 0.043 mg/ml, approximately half that of wild type (Table 5).

TABLE 5

Milk α-lactalbumin content.

| Source | α-lactalbumin (mg/ml) |
|---|---|
| Human | 2.9 ± 0.1(2) |
| α-lac$^m$/α-lac$^m$ mice | 0.09 ± 0.005(6) |
| α-lac-/α-lac-mice | 0(3) |
| α-lac$^m$/α-lac-mice | 0.043 ± 0.004(5) |
| α-lac$^m$/α-lac$^h$ mice | 0.65 ± 0.07(4) |
| α-lac$^h$/α-lac$^h$ mice | 1.38 ± 0.12(5) |

α-Lactalbumin content of milk samples were estimated by phenyl-Sepharose chromatography.

Values are means ±SE.

Figures in brackets indicate the number of mothers analysed.

α-Lactalbumin deficiency has no apparent effect on mammary gland development. Table 4 shows that total mammary tissue weights of wild type, heterozygous α-lac$^m$/α-lac- and homozygous α-lac-/α-lac- lactating mothers were not significantly different. Light microscopic analysis of mammary glands (FIG. 14) revealed that heterozygous and homozygous α-lac-/α-lac- glands were histologically normal. However, the alveoli and ducts of homozygous glands were distended and clogged with material rich in lipid droplets.

Replacement of mouse α-lactalbumin by human α-lactalbumin

We have generated mice carrying the human α-lactalbumin gene at the mouse α-lactalbumin locus. The 2.7 kb mouse α-lactalbumin fragment deleted at the α-lac-null allele was replaced by a 2.97 kb fragment containing the complete human α-lactalbumin coding region and 5' flanking sequences. The human fragment stretches from 0.77 kb upstream of the human transcription initiation site to an EcoRI site 136 bp 3' of the human translational stop site. Junctions with mouse sequences were made at a BamHI site 0.57 kb upstream of the mouse transcription initiation site and at an XbaI site 147 bp 3' of the mouse translational stop site (see Stacey et al, 1994, supra; see also FIG. 11). Here we describe our analysis of animals carrying this allele, designated α-lac$^h$.

Deletion of the murine α-lactalbumin gene established that α-lactalbumin deficiency blocks lactose synthesis and severely disrupts milk production. We have used the α-lac$^h$ allele to test the ability of human α-lactalbumin to restore milk production in the absence of mouse α-lactalbumin. α-lac$^m$/α-lac$^h$ heterozygous and α-lac$^h$/α-lac$^h$ homozygous mice were normal in appearance, fertility and behaviour.

In contrast to α-lac-/α-lac - mice, α-lac$^h$/α-lac$^h$ homozygous mothers produce apparently normal milk and rear offspring successfully. Table 4 shows that pups raised by α-lac$^h$/α-lac$^h$ heterozygous and α-lac$^h$/α-lac$^h$ homozygous females are similar in weight to those of wild type mothers. This is supported by our observation that these animals raised successive litters of pups entirely normally. These data constitute clear evidence that the human gene can functionally replace the mouse gene. Analysis of milk composition (Table 4) shows that lactose concentration is similar in all genotypes. Although both protein and fat concentrations seem reduced in α-lac$^h$/α-lac$^h$ homozygous animals, only the fat reduction was judged statistically significant by unpaired t-test. These animals show an increase in milk volume over wild type (Table 4).

Relative quantification of human and mouse α-lactalbumin RNA

Human milk contains considerably more α-lactalbumin (2.5 mg/ml) than murine milk (0.1 mg/ml). We wished to determine whether the human α-lactalbumin fragment retained a high level of expression when placed at the mouse locus, or assumed a lower level more characteristic of the mouse gene. α-lac$^m$/α-lac$^h$ heterozygous mice provided an ideal means of addressing this question, as the expression of the human gene could be directly compared with its mouse counterpart in the same animal.

FIG. 15A shows the strategy used to compare levels of mouse and human α-lactalbumin mRNA. Because the junction between human and mouse α-lactalbumin sequences lies upstream of the polyadenylation site, α-lac$^h$ mRNA contains a "tag" of 120 bases of untranslated mouse sequences at the 3' end. A uniformly radiolabelled mouse RNA probe was used in a ribonuclease protection assay to detect and distinguish human and mouse α-lactalbumin mRNA in the same RNA sample. The relative abundance of each mRNA was calculated from the amount of label in fragments protected by human and mouse mRNAs.

A ribonuclease protection assay was performed and the results are shown in FIG. 15B. Lane A shows the undigested 455 base probe and Lane K shows that yeast tRNA did not protect any fragments. Wild type mouse RNA protected a fragment consistent with the predicted 305 base RNA from endogenous mouse α-lactalbumin RNA (see Lane B). Homozygous α-lac$^h$/α-lac$^h$ gland RNA protected a smaller band consistent with the predicted 120 base RNA protected by human α-lactalbumin mRNA (see Lane C). Lanes D–J show results consistent with a series of heterozygous α-lac$^m$/α-lac$^h$ animals were obtained (see Lanes D to J). Small and large protected fragments in each sample indicate the presence of both human and mouse α-lactalbumin mRNA. Protected fragments were excised from the gel, radioisotope content measured, adjusted for the size difference and the ratio of human to mouse α-lactalbumin mRNA estimated. Table 6 shows the amount of radioisotope present in the 305 base and 120 base fragments excised from Lanes D to J of the gel shown in FIG. 15B, and the calculated ratio of human to mouse α-lactalbumin mRNA in each α-lac$^m$/α-lac$^h$ heterozygote. It is apparent that, although there was variation between individual animals, human α-lactalbumin mRNA was significantly more abundant than mouse mRNA. Averaging the seven α-lac$^m$/α-lac$^h$ heterozygotes gives a value of 15-fold greater expression for human α-lactalbumin mRNA.

TABLE 6

Relative quantification of human and mouse α-lactalbumin mRNA in α-lac$^m$/α-lac$^h$ mammary glands

| Lane | Mouse # | 120 base fragment[a] | 305 base fragment[a] | human/mouse RNA ratio[b] |
| --- | --- | --- | --- | --- |
| D | 2 | 5957 | 1000 | 15:1 |
| E | 3 | 5770 | 547 | 26:1 |
| F | 4 | 4825 | 810 | 15:1 |
| G | 76 | 6018 | 1077 | 14:1 |
| H | 98 | 5206 | 1452 | 9:1 |
| I | 99 | 5481 | 1117 | 12:1 |
| J | 79 | 26858 | 3561 | 19:1 |

Lane designations indicate the source of protected fragments and correspond to those shown in FIG. 15B.
[a]numbers are expressed in counts per minute (c.p.m.)
[b]Ratio between c.p.m. of 120 base fragment multiplied by 2.54 (to adjust for size difference) and c.p.m. of 305 base fragment.

Human α-lactalbumin protein expression

A Western analysis of α-lactalbumin in targeted mouse lines was conducted. Human α-lactalbumin can be distinguished from mouse α-lactalbumin by its faster electrophoretic mobility (see Lanes A, B). A prominent lower band in α-lac$^h$/α-lac$^h$ homozygotes and α-lac$^h$/α-lac$^m$ heterozygotes was observed (see Lanes C, D, G, H), and corresponds to the position of the human α-lactalbumin standard and was only observed in mice which express human α-lactalbumin generated either by gene targeting or by pronuclear microinjection (data not shown). This identity was confirmed by phenyl-Sepharose chromatography (See FIG. 16) and analysis of peptides released by cyanogen bromide cleavage (data not shown). The band with slower mobility, similar to mouse α-lactalbumin, is also a human α-lactalbumin gene product the nature of which is unknown. This species varied in intensity with α-lac$^h$ gene dosage (see Lanes G, H) and was also present in milk from human α-lactalbumin transgenic mice generated by pronuclear microinjection (data not shown).

The α-lactalbumin content of milk samples was quantified by phenyl-Sepharose chromatography. FIG. 16 shows superimposed absorbance profiles of column eluates of three illustrative milk samples including the α-lac$^m$/α-lac$^h$ heterozygote and α-lac$^h$/α-lalc$^h$ homozygote shown in FIG. 13. The peaks corresponding to eluted α-lactalbumin are marked. α-Lactalbumin contents were estimated by comparing the integrated peak areas with the human α-lactalbumin standard curve shown. The relationship between integrated peak area and α-lactalbumin quantity was linear and highly reproducible. α-Lactalbumin content for the samples shown in FIG. 16 were estimated as follows: α-lac$^m$/α-lac$^m$ wild-type 0.1 mg/ml; α-lac$^m$/α-lac$^h$ heterozygote #76 0.45 mg/ml; α-lac$^h$/α-lac$^h$ homozygote #22 0.9 mg/ml. Table 5shows the concentration of α-lactalbumin in milk samples from targeted mouse lines and lactating women. It is clear that the concentration of α-lactalbumin in milk is directly related to gene dosage, eg α-lac$^m$/α-lac-heterozygotes shown an α-lactalbumin concentration half that of wild type. Given that the volumes of milk produced by these mice are similar (Table 4), the concentration of α-lactalbumin provides a reasonable indication of the quantity synthesised. The relative proportions of human and mouse α-lactalbumin components in α-lac$^m$/α-lac$^h$ heterozygote milk were estimated by assuming that α-lactalbumin expression from a single mouse allele was 0.043 mg/ml and the rest represented human α-lactalbumin. This is consistent with the amounts of α-lactalbumin expressed by α-lac$^m$/α-lac-heterozygotes and wild type mice. Therefore, α-lac$^m$/α-lac-heterozygotes were estimated as expressing 0.61 mg/ml human and 0.043 mg/ml mouse α-lactalbumin. Thus, human α-lactalbumin is approximately 14-fold more abundant than mouse α-lactalbumin in α-lac$^m$/α-lac$^h$ heterozygote milk. This is remarkably consistent with the relative proportions of mRNA.

EXAMPLE 8

Enhanced expression of a heterologous gene

These data confirm that the upstream promoter region (AUG to about −3.7 kb) which is included in the pHA-2 construct enhances expression of a heterologous gene. Table 7 shows the results of milk analysis from pHA-2 transgenic founder females. Out of 10 females, 6 animals expressed high levels of human α-lac. 3 animals failed to express detectable levels of human α-lac (less than 0.2 mg/ml in this assay), all 3 also failed to transmit the transgene. We can neither be certain whether they were low expressors or not transgenic.

Table 8: Constructs PKU-0 to BALT-B all contain the bovine α-lac promoter (about 2 kb). Constructs PKU-1H to PKU-16 all contain the human α-lac promoter (3.7 kb). Using the human α-lac promoter increased the expression of the transgene to almost 100%.

These data show that the use of the human α-lac promoter achieves a higher level of expression than the use of the bovine promoter, and induces expression in more animals than the bovine promoter.

TABLE 7

| CONSTRUCT | MOUSE | SEX | C | mg/ml MILK ANALYSIS | TRANS. | MI FREQ. |
|---|---|---|---|---|---|---|
| pHA2 | 210-17 | M | | — | — | 1/21 = 5% |
| | 211-12 | F | <1 | — | — | 14/54 = 26% |
| | 211-16 | F | 10 | 5 | 3/4 | |
| | 211-17 | F | >>10 | ND | 0/8 | |
| | 211-24, 27, 29, 31, 36, 37, 42, 46, 47, 54 | M | | | | |
| | 212-7 | F | 10 | ND | 0/5 | 8/77 = 10% |
| | 212-11 | F | <10 | 1 | 0/4 | |
| | 212/13 | F | >1 | 1–5 | 2/4 | |
| | 212-19 | F | >10 | ND | 0/8 | |
| | 212-36, 44, 45, 46 | M | | | | |
| | 213-4 | F | <10 | 5 | 0/2 | 2/14 = 14% |
| | 213-5 | F | >10 | 10 | 2/8 | |

OVERALL MIF 25/166 = 15%
ND = Not detectable
TBA = To be analysed
TBO = To bred on
C = Copy number
TRANS. = Transmission
MI FREQ. = Integration frequency

TABLE 8

| Constr. | Transgenics | Expressers | max. expr. |
|---|---|---|---|
| PKU-0 | 6F/5M | 3/5 | 500 |
| PKU-1 | 18F/23M | 5/18 | 200 |
| PKU-2 | 8F/7M | 3/8 | 400* |
| PKU-3 | 6F/5M | 2/6 | 100* |
| PKU-4 | 7F/3M | 5/18 | 300* |
| BALT-A | 34F/24M | n.t. | n.t. |
| BALT-B | 10F/18M | n.t. | n.t. |
| PKU-1H | 6F/5M | 4/5 | 100 |
| PKU-5 | 13F/14M | 13/13 | 800 |
| PKU-6 | 3F/4M | 2/2 | 100 |
| PKU-7 | 4F/11M | 1/1 | <20 |
| PKU-16 | 13F/12M | n.t. | n.t. |
| HαPKU-1 | n.t. | n.t. | n.t. |
| HαPKU-2 | n.t. | n.t. | n.t. | n.t. — not tested
*estimate

We claim:

1. A method of producing non-human animal milk containing at least 2 mg/ml of an α-lactalbumin selected from the group consisting of:
   (i) human α-lactalbumin; and
   (ii) modified human α-lactalbumin having from one to four of the natural phenylalanine residues substituted by other amino acid residues;
said method comprising:
   (1) producing milk in the mammary gland of an adult transgenic, non-human placental mammal whose somatic and germ cells include a genetic construct comprising, in the 5' to 3' direction and operatively linked:
      (a) at least 1.8 kb of 5'-flanking sequence from the human α-lactalbumin gene including the α-lactalbumin promoter;
      (b) a DNA sequence encoding
         (1) a secretion signal; and
         (2) an α-lactalbumin selected from the group consisting of:
            (i) human α-lactalbumin; and
            (ii) modified human α-lactalbumin having from one to four of the natural phenylalanine residues substituted by other amino acid residues;
      (c) at least about 3 kb of 3'-flanking sequence from the human α-lactalbumin gene;
      wherein said construct is expressed in the mammary gland of said mammal and α-lactalbumin is produced in the milk at a level of at least 2 mg/ml; and
   (2) collecting the milk produced in step (1), wherein said milk contains at least 2 mg/ml of said human α-lactalbumin or said modified human α-lactalbumin.

2. A method of producing an α-lactalbumin selected from the group consisting of:
   (i) human α-lactalbumin; and
   (ii) modified human α-lactalbumin having from one to four of the natural phenylalanine residues substituted by other amino acid residues;
said method comprising producing, by the method of claim 1, non-human animal milk containing at least 2 mg/ml of said α-lactalbumin and extracting said α-lactalbumin from said milk.

3. A transgenic non-human mammal whose somatic and germ cells contain a transgene construct, said transgene construct comprising, in the 5' to 3' direction and operatively linked:
   (a) at least about 1.8 kb of 5'-flanking sequence from the human α-lactalbumin promoter:
   (b) a DNA sequence encoding
      (1) a signal sequence; and
      (2) a α-lactalbumin selected from the group consisting of:
         (i) human α-lactalbumin; and
         (ii) a modified human α-lactalbumin having from one to four of the natural phenylalanine residues substituted by other amino acid residues;
   (c) at least about 3 kb of 3'-flanking sequence from the human α-lactalbumin gene;

wherein said transgene construct is integrated into the genome of said mammal in such a way that said DNA sequence is expressed in the mammary gland of said mammal to produce α-lactalbumin in the milk of said mammal at a level of at least 2 mg/ml.

4. The transgenic non-human mammal of claim 3 wherein said mammal is a mouse.

5. The transgenic non-human mammal of claim 3 wherein said mammal is a cow.

* * * * *